(12) United States Patent
Kurth et al.

(10) Patent No.: US 6,383,739 B1
(45) Date of Patent: May 7, 2002

(54) METHOD OF IDENTIFYING COMPOUNDS CAPABLE OF ACTIVATING ISL PRODUCTION

(75) Inventors: Reinhard Kurth, Dreieich; Michael Baier, Frankfurt; Karin Metzner, Frankfurt; Albrecht Werner, Frankfurt, all of (DE)

(73) Assignee: Budesrepublik Deutschland Vertreten Durch Den Bundesminister, Bonn (DE)

( * ) Notice: Subject to any disclaimer, the term of this patent is extended or adjusted under 35 U.S.C. 154(b) by 0 days.

(21) Appl. No.: 09/353,362

(22) Filed: Jul. 15, 1999

Related U.S. Application Data

(62) Division of application No. 08/944,449, filed on Oct. 6, 1999, now Pat. No. 5,985,613, which is a continuation of application No. PCT/EP96/01486, filed on Apr. 4, 1996.

(30) Foreign Application Priority Data

Apr. 7, 1995 (DE) .......................................... 195 13 152
Aug. 18, 1995 (EP) ............................................ 95113013

(51) Int. Cl.⁷ ............................ C12Q 1/70; C12Q 3/00; C12Q 1/00; G01N 33/567; C12P 21/02
(52) U.S. Cl. .................. 435/5; 435/3; 435/4; 435/7.21; 435/69.5
(58) Field of Search ........................... 435/3, 4, 5, 7.21, 435/69.5

(56) References Cited

U.S. PATENT DOCUMENTS

| | | | |
|---|---|---|---|
| 4,778,750 A | * 10/1988 | Gottlieb ........................... | 435/5 |
| 4,853,332 A | 8/1989 | Mark et al. ............. | 435/252.33 |
| 4,937,189 A | 6/1990 | Davidow et al. ........... | 435/69.1 |
| 5,217,881 A | 6/1993 | Park ........................... | 435/69.5 |
| 5,252,479 A | 10/1993 | Srivastava ................ | 435/235.1 |
| 5,627,023 A | * 5/1997 | Bolognesi et al. ............. | 435/5 |
| 5,807,712 A | 9/1998 | Center et al. .............. | 435/69.5 |

OTHER PUBLICATIONS

Reynard et al., "Allele frequencies of polymorphisms of the tumours necrosis factor–alpha, interleukin–10, interferon–gamma and interleukin–2 genes in a north european caucasoid group from the U.K.", *Eur J Immunogenet*, Aug. 2000; 27(4):241–9; Abstract.
Hackstein et al., "Definition of human interleukin–4 receptor alpha chain haplotypes and allelic association with atopy markers.", *Hum Immunol*, Nov. 1999; 60(11):1119–27; Abstract.
Jeong et al., "Limited allelic polymorphism in the human interleukin–3 gene.", *Mol. Cell Probes*, Feb. 1998; 12(1):49–53; Abstract.
Matesanz, et al., "Glutamine and tetrapeptide repeat variations affect the bilogical activity of different mouse interleukin–2 alleles.", *Eur J Immunol*, Aug. 1996; 26(8):1675–82; Abstract.
Rhoades et al., "Allele–specific expression patterns of interleukin–2 and Pax–5 revealed by a sensitive single–cell RT–PCR analysis.", *Curr Biol*, Jun. 29, 2000; 10(13):789–92; Abstract.
Manzoli et al., "Allelic polymorphism of the interleukin–1 receptor antagonist gene in patients with acute or stable presentation of ischemic heart disease.", *Cardiologia*, Sep. 1999; 44(9):825–30; Abstract.
Reuter., "Interleukin–16 found to Inhibit HIV Replication", Dec. 7, 1995, B17.
Cruikshank et al., "Interleukin–16.", *J. Leukoc Biol*, Jun. 2000; 67(6):757–766; Summary.
Center et al., "Interleukin 16: implications for CD4 functions and HIV–1 progression.", *Immunol Today*, Jun. 2000; 21(6):273–80; Summary.
Maeda et al., "Interleukin–11, 12, 13, 14, 15, 16, 17, 18 (IL–11, 12, 13, 14, 15, 16, 17)", *Nippon Rinsho*, Nov. 1999; 57 Suppl:790–3; Summary.
Lee et al., "Possible pathogenic role of IL–16 on SLE: with reference to HIV–1 infection", *Ryumachi*, Oct. 1998, 38(5)747–51, Summary.
Famularo et al., "CD8 lymphocytes in HIV infection: helpful and harmful", *J Clin Lab Immunol*, 1997, 49(1):15–32; Summary.
Cruikshank et al., "Signaling and functional properties of interleukin–16", *Int Rev Immunol*, 1998; 16(5–6):523–40; Summary.
Center et al., "Interleukin–16", *Int J Biochem Cell Biol*, Nov. 1997; 29(1):1231–34; Summary.
Yang et al., "CD8+ cells in human immunodeficiency virus type I pathogenesis: cytolyti inhibition of viral replication", *Adv Immunol*, 1997; 66:273–311; Summary.
Center et al., "Interleukin 16 and its function as a CD4 ligand", *Immunol Today*, Oct. 1996; 17(10):476–81; Summary.
G. Kolata, The New York Times National Thursday, Dec. 7, 1995, B17, "2 Teams Report Natural Defenses Halt AIDS Virus in Lab.".
P. Recer, The News–Times, AP–DS–12–07–95, "Researchers Isolated Natural AIDS Fighters".
International Publication No. WO 95/07715 published Sep. 15, 1994.

(List continued on next page.)

Primary Examiner—Ali R. Salimi
Assistant Examiner—Bao Qun Li
(74) Attorney, Agent, or Firm—Arent Fox Kintner Plotkin Kahn

(57) ABSTRACT

The present invention is directed to an Immunodeficiency-virus Suppressing Lymphokine (ISL) produced by stimulated CD8+ PBMC, cloning and isolation of nucleic acid molecules for eukaryotic ISL, and methods of treating viral infections with ISL. ISL is able to suppress the replication of viruses, especially retroviruses, in vitro and in vivo. More, specifically, a method is described for detecting a compound capable of inducing the expression of ISL by measuring the presence of ISL and the ability of ISL to inhibit HIV transcription.

3 Claims, 3 Drawing Sheets

OTHER PUBLICATIONS

Figure 1:
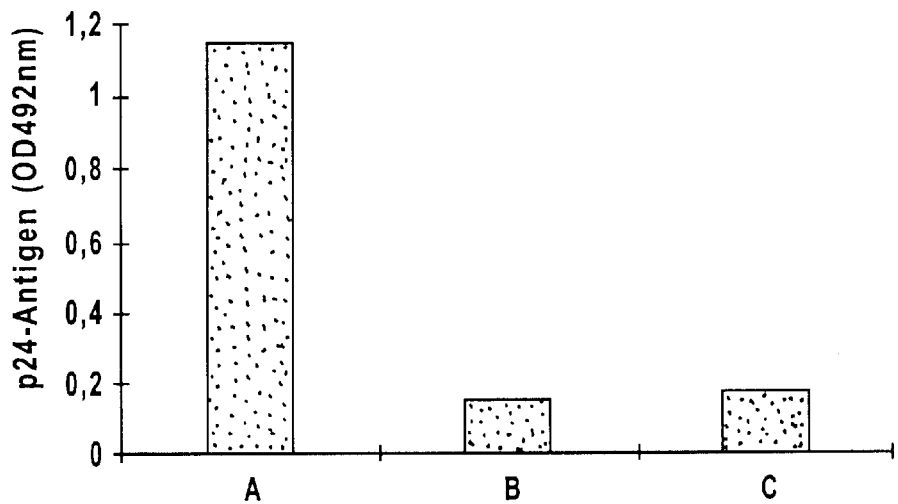

Proceedings of the National Academy of Sciences of USA, vol. 91, pp. 7207–7211 Jul. 1994, "CD8+ T lymphocytes of African green monkeys secrete an immunodeficiency virus–suppressing lymphokin." Ennen et al.

Reaserch in Immunology, vol. 145, No. 8–9, Jan. , 994, pp. 647–652, "The activated CD8 T–lymphocytes–derived immumodeficiency virus–suppressing lymphokine in African green monkeys . . . ". Ennen et al.

Immunology, vol. 66, Apr. 1989, pp. 628–630, "A diffusible lymphokine produced by CD8+ T lymphocytes suppresses HIV replication." Walker et al.

International Publication No. WO 94/28134 published Dec. 8, 1994.

Proceeding of the National Academy of Sciences of USA, vol. 91, pp. 5109–5113, May 1994, Molecular and functional analysis of a lymphocyte chemoattractant factor: Association of biologic function . . . Cruikshank et al.

The Journal of Laboratory and Clinical Medicine, vol. 125, No. 2, Feb. 1995, pp. 167–171, "The Lymphocyte Chemoattractant Factor". Center et al.

Nature, vol. 378, Dec. 7, 1995, pp. 563, "HIV suppression by Interleukin–16". Baier et al.

* cited by examiner

Fig.3a

```
        1                                                    10                                                  20                                                  30              35
a) · ATG CCC GAC CTC AAC TCC ACT GAC TCT GCA GCC TCA GCC AGT GAT GTT TCT GTA GAA TCT ACA GCA GAG GCC ACA GTC TGC ACG GTG ACA CTG
     Met Pro Asp Leu Asn Ser Thr Asp Ser Ala Ala Ser Ala Ser Asp Val Ser Val Glu Ser Thr Ala Glu Ala Thr Val Cys Thr Val Thr Leu
b) · *** *** *** *** *** *** *** *** *** *** *** *** *** *** *** *** **G *** *** *** *** *** *** *** *** *** *** *** *** ***
     Met Pro Asp Leu Asn Ser Thr Asp Ser Ala Ala Ser Ala Ser Asp Val Ser Val Glu Ser Thr Ala Glu Ala Thr Val Cys Thr Val Thr Leu
c) · * * * * * * * * * * * * * * * * * * * * C T * * * * * * * * ***
     Met Pro Asp Leu Asn Ser Thr Asp Ser Ala Ala Ser Ala Ser Asp Val Ser Val Glu Ser Ala Glu Ala Thr Val Tyr Thr Val Thr Leu
d) · * * * * * * A T * * * * * * * * * * * * C T * * * * *A* * * * *
     Met Pro Asp Leu Asn Ser Thr Thr Asp Ser Ala Ala Ser Ala Ser Asp Val Ser Val Glu Ser Ala Glu Ala Thr Val Tyr Thr Val Thr Leu
e) · * * * * * * A T * * * * * * * * * * * * C T * * * * *A* * * * *
     Met Pro Asp Leu Asn Ser Thr Thr Asp Ser Ala Ala Ser Ala Ser Asp Val Ser Val Glu Ser Ala Glu Ala Thr Val Tyr Thr Val Thr Leu
f) · * * * * * * A T * * * * * * * * * * * * C T * * * * *A* *  A * *
     Met Pro Asp Leu Asn Ser Thr Thr Asp Ser Ala Ala Ser Ala Ser Asp Val Ser Val Glu Ser Ala Glu Ala Thr Val Tyr Thr Val Thr Leu
g) · * * * * * * A T * * * * * * * * * * * * C T * * * * *A* * * * *
     Met Pro Asp Leu Asn Ser Thr Thr Asp Ser Ala Ala Ser Ala Ser Asp Val Ser Val Glu Ser Ala Glu Ala Thr Val Tyr Thr Val Thr Leu 36                                                  40                                                  50                                                  60                                                  70
a) · GAG AAG ATG TCG GCA GGG CTG GGC TTC AGC CTG GAA GGA GGG CTC CTA CAC GGA GAC AAG CCT CTC ACC ATT AAC AGG ATT TTC AAA GGA GCA GCC TCA
     Glu Lys Met Ser Ala Gly Leu Gly Phe Ser Leu Glu Gly Gly Lys Gly Lys Gly Ser Leu His Gly Asp Lys Pro Leu Thr Ile Asn Arg Ile Phe Lys Gly Ala Ala Ser
b) · *** *** *** *** *** *** *** *** *** *** *** *** *** *** *** *** *** *** *** *** *** *** *** *** *** *** *** *** *** *** *** *** *** *** *** ***
     Glu Lys Met Ser Ala Gly Leu Gly Phe Ser Leu Glu Gly Gly Lys Gly Lys Gly Ser Leu His Gly Asp Lys Pro Leu Thr Ile Asn Arg Ile Phe Lys Gly Ala Ala Ser
c) · *** *** *** *** *** *** *** *** *** **T *** *** *** *** *** *** *** *** *** *** **G *** *** *** *** *** *** *** *** *** *** *** *** *** *** ***
     Glu Lys Met Ser Ala Gly Leu Gly Phe Ser Leu Glu Gly Gly Lys Gly Lys Gly Ser Leu His Gly Asp Lys Pro Leu Thr Ile Asn Arg Ile Phe Lys Gly Ala Ala Ser
d) · *** *** *** *** *** *** *** *** *** **T *** *** *** *** *** *** *** *** *** *** **G *** *** *** *** *** *** *** *** *** *** *** *** *** *** ***
     Glu Lys Met Ser Ala Gly Leu Gly Phe Ser Leu Glu Gly Gly Lys Gly Lys Gly Ser Leu His Gly Asp Lys Pro Leu Thr Ile Asn Arg Ile Phe Lys Gly Ala Ala Ser
e) · *** *** *** *** *** *** *** *** *** **T *** *** *** *** *** *** *** *** *** *** **G *** *** *** *** *** *** *** *** *** *** *** *** *** *** ***
     Glu Lys Met Ser Ala Gly Leu Gly Phe Ser Leu Glu Gly Gly Lys Gly Lys Gly Ser Leu His Gly Asp Lys Pro Leu Thr Ile Asn Arg Ile Phe Lys Gly Ala Ala Ser
f) · *** *** *** *** *** *** *** *** *** **T *** *** *** *** *** *** *** *** *** *** **G *** *** *** *** *** *** *** *** *** *** *** *** *** *** ***
     Glu Lys Met Ser Ala Gly Leu Gly Phe Ser Leu Glu Gly Gly Lys Gly Lys Gly Ser Leu His Gly Asp Lys Pro Leu Thr Ile Asn Arg Ile Phe Lys Gly Ala Ala Ser
g) · *** *** *** *** *** *** *** *** *** *** *** *** *** *** *** *** *** *** *** *** **G *** *** *** *** *** *** *** *** *** *** *** *** *** *** ***
     Glu Lys Met Ser Ala Gly Leu Gly Phe Ser Leu Glu Gly Gly Lys Gly Lys Gly Ser Leu His Gly Asp Lys Pro Leu Thr Ile Asn Arg Ile Phe Lys Gly Ala Ala Ser
```

Fig.3b

```
    71                                    80                                                90                                               100
a). GAA CAA AGT GAG ACA GTC CAG CCT GGA GAT GAA ATC TTG CAG GCT GGC ACT GCC ATG CAG GGC CTC ACA CGG TTT GAA GCC TGG AAC
    Glu Gln Ser Glu Thr Val Gln Pro Gly Asp Glu Ile Leu Gln Leu Gly Gly Thr Ala Met Gln Gly Leu Thr Arg Phe Glu Ala Trp Asn
b). *** *** *** *** *** *** *** *** *** *** *** *** *** *** *** *** *C* *** *** *** *** *** *** *** *** *** *** *** *** ***
    Glu Gln Ser Glu Thr Val Gln Pro Gly Asp Glu Ile Leu Gln Leu Ala Gly Thr Ala Met Gln Gly Leu Thr Arg Phe Glu Ala Trp Asn
c). *** *** *** *** *** A** *** *** *** *** *** *** *** *** *** *** *C* *** *** *** *** *** *** *** *** *** *** *** *** ***
    Glu Gln Ser Glu Thr Ile Gln Pro Gly Asp Glu Ile Leu Gln Leu Ala Gly Thr Ala Met Gln Gly Leu Thr Arg Phe Glu Ala Trp Asn
d). *** *** *** *** *** A** *** *** *** *** *** *** *** *** *** *** *C* *** *** *** *** *** *** *** *** *** *** *** *** ***
    Glu Gln Ser Glu Thr Ile Gln Pro Gly Asp Glu Ile Leu Gln Leu Ala Gly Thr Ala Met Gln Gly Leu Thr Arg Phe Glu Ala Trp Asn
e). *** *** *** *** *** A** *** *** *** *** *** *** *** *** *** *** *C* *** *** *** *** *** *** *** *** *** *** *** *** ***
    Glu Gln Ser Glu Thr Ile Gln Pro Gly Asp Glu Ile Leu Gln Leu Ala Gly Thr Ala Met Gln Gly Leu Thr Arg Phe Glu Ala Trp Asn
f). *** *** *** *** *** A** *** *** *** *** *** *** *** *** *** *** *C* *** *** *** *** *** *** *** *** *** *** *** *** ***
    Glu Gln Ser Glu Thr Ile Gln Pro Gly Asp Glu Ile Leu Gln Leu Ala Gly Thr Ala Met Gln Gly Leu Thr Arg Phe Glu Ala Trp Asn
g). *** *** *** *** *** *** *** *** *** *** *** *** *** *** *** *** *C* *** *** *** *** *** *** *** *** *** *** *** *** ***
    Glu Gln Ser Glu Thr Val Gln Pro Gly Asp Glu Ile Leu Gln Leu Ala Gly Thr Ala Met Gln Gly Leu Thr Arg Phe Glu Ala Trp Asn 101                                   110                                              120                                              130
a). ATC ATC AAG GCA CTG CCT GAT GGA CCT GTC ACG ATT GTC ATC AGG AGA AAA AGC CTC CAG TCC AAG GAA ACC ACA GCT GGA GAC TCC TAG
    Ile Ile Lys Ala Leu Pro Asp Gly Pro Val Thr Ile Val Ile Arg Arg Lys Ser Leu Gln Ser Lys Glu Thr Thr Ala Ala Gly Asp Ser -
b). *** *** *** *** *** *** *** *** *** *** *** *** *** *** *** **G *** *** *** *** *** *** *** *** *** *** *C* *** *** ***
    Ile Ile Lys Ala Leu Pro Asp Gly Pro Val Thr Ile Val Ile Arg Arg Lys Ser Leu Gln Ser Lys Glu Thr Thr Ala Ala Gly Asp Ser -
c). *** *** **C *** *** *** *** *** *** *** *** *** *** **A **T *** **G *** *** *** *C* *** *** *** *** *** *C* *** *** ***
    Ile Ile Lys Ala Leu Pro Asp Gly Pro Val Thr Ile Val Ile Arg Arg Lys Ser Leu Gln Pro Lys Glu Thr Thr Ala Ala Gly Asp Ser -
d). *** *** **C *** *** *** *** *** *** *** *** *** *** **A **T *** **G *** *** *** *C* *** *** *** *** *** *C* *** *** ***
    Ile Ile Lys Ala Leu Pro Asp Gly Pro Val Thr Ile Val Ile Arg Arg Lys Ser Leu Gln Pro Lys Glu Thr Thr Ala Ala Gly Asp Ser -
e). *** *** **C *** *** *** *** *** *** *** *** *** *** **A **T *** **G *** *** *** *C* *** *** *** *** *** *C* *** *** ***
    Ile Ile Lys Ala Leu Pro Asp Gly Pro Val Thr Ile Val Ile Arg Arg Lys Ser Leu Gln Pro Lys Glu Thr Thr Ala Ala Gly Asp Ser -
f). *** *** **C *** *** *** *** *** *** *** *C* *** *** **A **T *** **G *** *** *** *C* *** *** *** *** *** *C* *** *** ***
    Ile Ile Lys Ala Leu Pro Asp Gly Pro Val Thr Ile Val Ile Arg Arg Lys Ser Leu Gln Pro Lys Glu Thr Thr Ala Ala Gly Asp Ser -
g). * * C * * * * * * * * * * A T * G * * * A C * * * * *C* * * ***
    Ile Ile Lys Ala Leu Pro Asp Gly Pro Val Thr Ile Val Ile Arg Arg Lys Ser Leu Gln Pro Lys Glu Thr Thr Ala Ala Gly Asp Ser -
```

METHOD OF IDENTIFYING COMPOUNDS CAPABLE OF ACTIVATING ISL PRODUCTION

This application is a divisional application filed under 37 CFR §1.53(b) of parent application Ser. No. 08/944,449, filed Oct. 6, 1997, now U.S. Pat. No. 5,985,613 which is a continuation of PCt/EP96/01486 filed Apr. 4, 1996.

The present invention concerns the use of an "immunodeficiency-virus suppressing lymphokine (ISL)" to inhibit the replication of viruses, therapeutic compositions containing ISL or nucleic acid molecules coding therefor.

ISL activity is defined by inhibition of HIV replication on primary lymphocytes (PBMC).

It is known that certain $CD8^+$ cells, e.g., those of human and animal origin which, in addition to being $CD8^+$ are $HLA-DR^+$, $CD28^+$, or $CD11B^-$, show activity in suppressing immunodeficiency viruses, such as HIV and SIV. This activity has been attributed to a molecule referred to as immunodeficiency virus suppressing lymphokine or "ISL". ISL is capable of inhibiting the replication of viruses in $CD4^+$ cells that are infected with HIV or SIV (Ennen, Findeklee, Kurth et al (Proc. Natl. Acad. Sci. USA, Vol. 91, p. 7207–7211 (1994). However, the identity of ISL has to date been unclear. It has been known since at least 1989 (Walker, C. M., and Leighly, J. A., Immunology, Vol. 66, p. 628–630 (1989)) that there exists a soluble factor secreted by stimulated human $CD8^+$ T lymphocytes that downregulates HIV replication in $CD4^+$ T cells. However, it has until now been impossible to establish whether this activity results from a single substance, and it has also until today even been impossible to isolate and characterize a substance with this activity although there exist a lot of publications in which methods of setting up corresponding cell cultures are described and methods of purifying such antiviral factors are suggested. Such publications are, e.g., WO 94/23058 and WO 93/0883 as well as by Mackewicz et al (Lancet, 344, p. 1671–1673 (1994)); Mackewicz et al (AIDS Research and Human Retroviruses, Vol. 8, No. 6, p. 1039–1050 (1992); Castro, Walker et al (Cellular Immunology 132, p. 246–255, (1991); Blackbourn et al (Journal of Medical Primatology No. 23, p. 343–354 (1994); Chen et al (AIDS Research and Human Retroviruses Vol. 9, No. 11, p. 1079–1086)); Kannagi et al (The Journal of Immunology, Vol. 140, No. 7, p. 2237–2242 (1988)); Joag et al (Virology 200, p. 436–446 (1994)); Walker, Moody et at (Science, Vol. 234, p. 1563–1566 (1986)); Walker, Erickson et al (Journal of Virology, Vol. 65, No. 11, p. 5921–5927 (1991)); Walker, Thomson-Honnebier et al (Cellular Immunology 137, p. 420–428 (1991)); Knuchel, Bednarik et al (Journal of Acquired Immune Deficiency Syndromes, No. 7, p. 438–446 (1994)); Ennen, Findeklee, Kurth et al (Proc. Natl. Acad. Sci. USA, Vol. 91, p. 7207–7211 (1994)) and Hsueh, Walker et al (Cellular Immunology 159, p. 271–279 (1994)).

In spite of the above-mentioned intensive investigation that has been carried out on the immunodeficiency virus-suppressing activities produced from $CD8^+$ cells for about seven years, the biological nature (especially the molecular structure of ISL), apart from the assumption that ISL is a protein, is completely unclear. Also unclear are:

its gene or genes if it consists of several factors;
the way in which it acts on infected and non-infected $CD4^+$ cells. There are preliminary indications that the action of ISL is based on a negative regulation of the transcription rate of HIV-LTR (long terminal repeat);
its mechanism of action in other infections. It may be assumed that viruses whose transcription is regulated by transcription factors that are comparable to those of HIV will also be subjected to a negative regulation by ISL;
its mechanism of action on normal and malignant cell proliferation. According to the present state of knowledge it cannot be ruled out that, similar to the interferons, an inhibitory effect on normal or malignant cell proliferation may be possible;
the fact whether ISL could regulate CD4 expression;
why in the case of HIV-infected patients a decrease in the ISL activity that is measurable in vitro occurs over time;
the fact whether ISL may also be partly responsible for the long latency period between infection and development of disease in humans infected with HIV, i.e., be positively correlated with a positive prognosis.

The problem has therefore arisen of identifying ISL and to clarify whether it represents one or several substances as well as to examine it with regard to its therapeutic action on immunodeficiency viruses and other viruses.

Cruikshank and Center (Journal of Immunology 128 (1982) 2569–2574) describe a protein called "lymphocyte chemoattractant factor" (LCF), which has a sequence quite similar to the sequence of the polypeptides of the invention. It is expressed by human lymphocytes and is a member of the group of lymphokines. After appropriate purification by gel filtration a homogeneous product was obtained with a molecular weight of approximately 56,200 which is cleaved by sodium dodecyl sulphate into monomers with a molecular weight of ca. 14,400. It was assumed that this lymphokine played a role in the formation and amplification of the delayed type of immune response (delayed type hypersensitivity reaction).

The nucleic acid sequence of LCF is described by Cruikshank, W., et al., Proc. Nat. Acad. Sci. USA 91 (1994) 5109–5113. The nucleotide sequence and the protein sequence derived therefrom are available under Accession Number M90391 at GenBank data base and are shown in SEQ ID NO:3 and SEQ ID NO:4.

From Cruikshank et al (Journal of Immunology 138, 3817–3823 (1987)) it is also known that LCF stimulates the expression of interleukin 2 (IL2) receptors and HLA-DR antigens on $CD4^+$ lymphocytes. LCF is therefore also referred to as growth factor. Furthermore Cruikshank et al described in the Journal of Immunology 146, 2928–2934 (1991) that LCF induces CD4-dependent intracytoplasmic signals in lymphocytes and thus concluded that these signals act as a second type of messengers. In the J. Exp. Med. 173, p. 1521–1528 (1991) Rand, Cruikshank et al additionally describe the stimulation of human eosinophils by LCF and its massive production by activated T-lymphocytes. Finally in Proc. Natl. Acad. Sci. USA, Vol. 91, p. 5109–5113 (1994) Cruikshank et al described a cloning of LCF by isolating the LCF cDNA from an expression library from mitogen-stimulated mononuclear blood cells (PBMC: peripheral blood mononuclear cells) and introduction into E. coli to produce biologically active recombinant LCF protein (rLCF). Recombinant LCF shows an isoelectric point of 9.0 (Center, D. M., et al., J. Lab. Clin. Med. 125 (1995) 167–171).

Cruikshank, W., et al. (Proc. Nat. Acad. Sci. USA 91 (1994) 5109–5113) describes that LCF may contribute to recruitment of eosinophils and $CD4^+$ mononucleic cells concomitantly in intracellular reactions. Cruikshank further suggests that LCF activity on $CD4^+$ cells would provide a mechanism for the accumulation of non-sensitized T cells in tissue. Its ability to prime $CD4^+$ T cells for IL-2 responsiveness might play a role in the specific expansion of this T cell population. In WO 94/28134 the same authors suggest to use LCF as an immunosuppressive agent or as part of an immunosuppressive therapy. However, an antiviral activity of LCF was neither described in nor obvious from these publications. To the contrary, Center, D. M., et al., (1995) (supra) conclude that LCF does amplify the inflammatory process.

SUMMARY OF THE INVENTION

The subject-matter of the invention is the identification and molecular cloning of an immuno-deficiency-virus suppressing lymphokine (ISL) and the isolation of nucleic acid molecules which encode polypeptides with ISL activity. Such polypeptides have improved properties, especially a higher activity than the polypeptide described in WO 94/28134. More specifically, the invention relates to those nucleic acid molecules which encode eukaryotic ISL, including human, monkey and other species. Specifically preferred are nucleic acid molecules which hybridize to SEQ ID NO:1 under stringent conditions as set forth below and code for a polypeptide with ISL activity. It can be shown that natural, synthetic, and recombinantly produced ISL is able to suppress the replication of viruses, especially of retroviruses, in vivo and in vitro.

The nucleotide sequences according to the invention encode a polypeptide that binds to CD4$^+$ lymphocytes and can suppress the replication of viruses such as, in particular, HIV-1, HIV-2 and SIV strains. Therefore, such polypeptides, active fragments and derivatives also are a subject-matter of the present invention. The function of ISL is not limited by its presentation in an MHC complex.

A further subject-matter of the invention is the use of ISL for the therapeutic treatment of viral infections, preferably retroviral infections and/or viral-based benign and malignant diseases, and its use for the production of a therapeutic composition containing ISL, as well as its use for the manufacture of such therapeutic agents.

A further subject-matter of the invention is a therapeutic composition containing ISL in an amount effective for treatment of such diseases, especially viral infections. The pharmaceutical composition or agent also contains suitable pharmaceutically compatible carrier substances.

A further subject-matter of the invention is a polyclonal or monclonal anti-ISL antibody or an immuno-active fragment thereof, as well as methods for producing such antibodies and their use for ISL determination and detection of viral infections of eukaryotic cells, especially mammalian samples, preferably derived from mammalian cells.

Another subject-matter of the invention is the use of ISL for the detection of virus-activated mammalian cells, especially T cells.

A further subject-matter of the invention is a method for the determination of soluble or insoluble, free or cell-bound ISL. Such a diagnostic method can be used for the detection of acute or chronic infections, for monitoring the course of viral infections and/or for the monitoring and detection of viral-based benign and malignant diseases.

A further subject-matter of the invention is the use of a nucleotide molecule which can secure expression of ISL in a eukaryotic cell for the activation of ISL in human cells, for in vivo or ex vivo gene therapy.

Another subject-matter of the invention is a therapeutic composition useful in treating a pathological condition characterized by viral replication, especially retroviral replication, comprising at least a substance which activates ISL activity in CD8$^+$ T cells, and a pharmaceutically acceptable carrier.

Therefore, a further subject-matter of the invention is a method for the production of a substance and a therapeutic agent for inhibition of the replication of viruses in a patient, said method comprising combining with a pharmaceutically acceptable carrier a therapeutically effective amount of a substance which activates expression of a protein with ISL activity, preferably of a protein with the amino acid sequence shown in SEQ ID NO:2 in CD8$^+$ T cells, in vivo and in vitro, to such an extent that viral replication in CD4$^+$ cells is inhibited.

A further subject-matter of the invention is a therapeutic composition useful in treating a pathological condition characterized by viral replication, especially retroviral replication, comprising at least a substance which activates ISL activity in CD8$^+$ T cells, and a pharmaceutically acceptable carrier.

DETAILED DESCRIPTION OF THE INVENTION

The invention is based on new isolated polypeptides with ISL activity which inhibit the replication of HIV-1, preferably HIV-1$_{SF2}$ in CD8$^+$-depleted peripheral blood lymphocytes (PBMC) which are prepared from buffy coat of non-retrovirally infected normal human blood samples in an assay (also referred to in the following as an HIV inhibition assay), a) whereby said CD8$^+$-depleted PBMC are incubated with 0.1 μg of said polypeptide/1.5×10$^6$ cells in 150 μl medium for half an hour at 37° C.;

b) said CD8$^+$-depleted PBMC are subsequently infected with HIV-1, preferably with HIV-1$_{SF2}$ by incubating 1.5×10$^6$ cells in 150 μl with 50 μl HIV-1 stock solution containing 50 tissue infectious doses 50 (TCID$_{50}$) for 1 h at 37° C.;

c) said infected CD8$^+$-depleted PBMC are washed to remove unbound HIV-1 and, preferably, polypeptide;

d) CD8$^+$-depleted PBMC are cultivated at 37° C. in a 5% CO$_2$ atmosphere and medium is changed and said polypeptide is added after 3, 6, 9, and 12 days;

e) the amount of HIV-1 in the CD8$^+$-depleted PBMC cell culture supernatants is determined at days 9 and 12 post infection by serially threefold dilutions of supernatant and inoculation in quadruplicate wells onto 2000 cells in 150 μl medium of a highly susceptible indicator cell line, which must be routinely infectable to an extent of 85% or greater with said HIV-1 strains, preferably the human HTLV-transformed lymphoma cell line MT4;

f) virus replication in each well is determined 8 days post infection by determination of the reverse transcriptase (RT) in the cell culture supernatant (there is preferably applied the Reverse Transcriptase Assay of Boehringer Mannheim GmbH, Biochemica, 68298 Mannheim, Germany, Order No.: 1468 120) of every single well following the instructions of the manufacturer);

g) the tissue culture infectious doses 50 (TCID$_{50}$) of the CD8$^+$-depleted PBMC cultures is calculated preferably following the method published by Karber (Karber, G. 1931. Assay for statistical analysis of pharmacological experiments. Arch. Exper. Path. V. Pharmakol. 162, 148) according to the formula:

$$\log TCID_{50} = L - d(s - 0.5),$$

wherein

L=log of the lowest virus dilution d=log of virus dilution s=sum of virus-positive cell cultures;

h) inhibition of HIV-1 replication in the CD8⁺-depleted PBMC cultures is calculated by comparison of virus content of cell culture supernatants in an assay according to steps a) to g) and the virus content of an assay according to steps a) to g) where said polypeptide to be tested for inhibition of HIV replication is replaced by buffer without polypeptide (untreated control);

i) inhibition is found if the amount of viral replication in CD8⁺-depleted PBMC is inhibited in such a way that the amount of virus is about 50% or less, more preferably 10% or less, most preferably 1% or less in comparison to the untreated control, and the polypeptide i) is coded by the DNA sequence shown in SEQ ID NO:1 or a sequence complementary to the sequence shown in SEQ ID NO:1, ii) is coded by a DNA sequence which hybridizes with SEQ ID NO:1 or SEQ ID NO:3 or which hybridizes with a DNA sequence complementary to SEQ ID NO:1 or SEQ ID NO:3, under stringent conditions, iii) is coded by DNA sequences which, if there was no degeneracy of the genetic code, would hybridize under stringent conditions with the sequences defined in i) or ii), with the proviso that the polypeptide differs from the polypeptide coded by the DNA sequence shown in SEQ ID NO:3.

Useful polypeptides with ISL activity besides the preferred polypeptides of SEQ ID NO:2 or SEQ ID NO:4 are, for example, the also preferred polypeptides of FIG. 3. FIG. 3 also shows DNA sequences which code for these polypeptides. A further preferred polypeptide is a polypeptide according to the invention wherein amino acid 26 (alanine) is deleted. Such a polypeptide also exists as natural allelic forms in humans and monkeys.

In the examples which follow, a strain of HIV-1 known as HIV-1$_{SF2}$ is used. This is a typical North American/European strain. Its nucleotide sequence is set forth in SEQ ID NO:7, and is also accessible via GenBank Accession Number K02007. Other HIV strains include HIV-1$_{SF33}$ (SEQ ID NO:8), as well as strains set forth in, e.g., Cheng-Mayer et al., J. Virol 64 (1990) 4390–4398; Levy, J. A., et al., Science 232 (1986) 998–1001; Luciw, P. A., et al., Nature 312 (1984) 760–763; Sanchez-Pescador, R., et al., Science 227 (1985) 484–492.

In the assay applied for determination of ISL activity, Ficoll gradient purified and phytohaemagglutinin (PHA) stimulated PBMC were infected with an HIV-1 strain and cultivated. CD8⁺-depleted PBMC are used because of improved accuracy compared to the use of PBMC. However, it is also possible to use PBMC. CD8⁺-depleted cells are selected by cell sorting using specific antibodies. Such methods are widely known state of the art. The culture supernatants are tested for their virus content. For this purpose, e.g., determination of the reverse transcriptase or P24 antigen can be carried out. Another possibility is to determine the level of infection of highly susceptible indicator cell lines, referred to a virus-free cell supernatant in each case. In such a test, ISL activity will be found if the substance to be tested causes a reduction of reverse transcriptase activity for at least about 50%, preferably 70%, more preferably 90%, or more.

The polypeptide can be defined by its DNA sequence and by the amino acid sequence derived therefrom. The ISL polypeptide can occur in natural allelic variations which differ from individual to individual. Such variations of the amino acids are usually amino acid substitutions. However, they may also be deletions, insertions or additions of amino acids to the total sequence. The ISL protein according to the invention—depending, both in respect of the extent and type, on the cell and cell type in which it is expressed—can be in glycosylated or non-glycosylated form. Polypeptides with ISL activity can easily be identified by the above-described HIV inhibition assay.

FIG. 3 shows a comparison of the DNA and polypeptide sequences of human and different monkey ISL. It was found furthermore that an allelic variant wherein codon 26 (coding for Ala) is deleted exists in all of these species. As can be seen from FIG. 3, ISL polypeptides and nucleic sequences coding therefor, wherein amino acid 7 is Ser or Thr, amino acid 25 is Thr or Ser, amino acid 31 is Cys or Tyr, amino acid 76 is Val or Ile, amino acid 86 is Gly or Ala, amino acid 112 is Ile or Thr, amino acid 121 is Ser or Pro and/or amino acid 128 is Gly or Ala, are preferred. There are also preferred polypeptides in which amino acid 26 is deleted. Such variations can improve the antiviral tumor therapeutic (benign or malignant) and/or immunosuppressive activity of ISL without changing the biological properties in general.

"Polypeptide with ISL activity or ISL" means also proteins with minor amino acid variations but with substantially the same ISL activity. Substantially the same means that the activities are of the same biological properties and the polypeptides show preferably at least 75% homology in amino acid sequence. More preferably, the amino acid sequences are at least 90% identical.

"Indicator cell line" means as lymphoma cell line which must be routinely infectable to an extent of 85% or greater with the HIV-1 strain which is used in the HIV inhibition assay. Preferably, such an indicator cell line is MT4 which is described in Norley, S. G., et al, Biologicals 21 (1993) 251–258 which is incorporated herein by reference. Other useful lymphoma cell lines are described by Cheng-Mayer, C., et al, Virol. 181 (1991) 288–294 and J. Virol. 65 (1991) 6931–6941 which also are incorporated herein by reference. In these publications there are described lymphoma cell lines which are infectable by HIV-1 to a greater or lesser extent. From the named cell lines only those cell lines which are routinely injectable to an extent of 85% or greater with the HIV strain of the HIV inhibition assay are useful.

"ISL activity" denotes the anti-viral action of the tissue culture supernatant of activated and non-activated CD8⁺ lymphocytes of human (ISL) or animal origin (e.g. ISL in the lymphocytes of African green monkeys (ISL-agm)).

"ISL" preferably denotes the molecule whose sequence is shown in SEQ ID NO:1, 2, 3, or 4.

ISL is a polypeptide which is active in its glycosylated or unglycosylated form. The unglycosylated form can be produced by recombinant technology in prokaryotic cells.

ISL is produced by non-activated (small amount) as well as by activated T lymphocytes. ISL binds to CD4⁺ lymphocytes, preferably to the CD4 receptor molecule or to a molecule associated with the CD4 molecule. ISL has suppressed the replication of all HIV-1 and HIV-2 strains tested up to now as well as all previously tested SIV strains. This effect can be observed on CD4⁺-lymphocytes from peripheral blood as well as in a number of human CD4⁺-positive T cell lymphomas. ISL has an interspecies-specific action since at least the ISL of the African green monkey is capable of suppressing the replication of HIV in human CD4+ cells. The function of ISL is not limited by an incompatibility of the MHC locus (major histocompatibility complex) and it does not have a lytic action on cells. ISL is synthesized by the CD8+ lymphocytes of asymptomatic patients infected with HIV and less by cells from symptomatic patients. ISL is also produced by activated CD8+ cells of healthy blood donors. The extent of ISL synthesis correlates quantitatively with the clinical status of HIV-infected patients. The ISL activity in asymptomatic HIV patients is higher (with a comparable number of activated CD8+ lymphocytes) than in symptomatic patients. The antiviral action of ISL is not identical with previously known lymphokines and interferons. ISL activity has also been detected in the cell culture supernatant of activated CD8+ lymphocytes of HIV-infected and non-infected chimpanzees as well as of SIV-infected and non-infected African green monkeys, Rhesus monkeys and Sooty mangabees (Ennen, J., et al, Proc. Natl. Acad. Sci. USA 91 (1994) 7207–7211). ISL may be capable of protecting against superinfections with other HIV/SIV strains (Cheng-Mayer, C., et al, J. Virol. 64 (1990) 4390–4398).

A protein with ISL activity is described in Cruikshank et al, Proc. Natl. Acad. Sci. USA 91 (1994) 5109–5113 and WO 94/28134 and is named LCF (see supra). This protein is coded by SEQ ID NO:3 and therefore has the sequence SEQ ID NO:4. Cruikshank refers, for the sequence reported to Accession Number M90391 accorded by GenBank data base. Whereas the protein sequences shown in GenBank and FIG. 2 of Cruikshank are identical, the nucleic acid sequences exhibit a difference in nucleotide 1070. Whereas in the GenBank sequence this nucleotide is T, in FIG. 2 of Cruikshank's publications this nucleotide is G. As TTG does not code for Phe but for Leu, it is clear that G is a typographical error. This is confirmed by cloning of ISL cDNA derived from independent PCR amplifications. From these clones it is clear that the LCF sequence in codon 96 is indeed represented by the sequence TTT. Therefore, nucleotide 1070 clearly is T.

The term "nucleic acid molecule" denotes a polynucleotide which can be, for example, a DNA, RNA, or derivatized active DNA or RNA. DNA and/or RNA molecules are preferred, however.

The term "hybridize under stringent conditions" means that two nucleic acid fragments are capable of hybridization to one another under standard hybridization conditions described in Sambrook et al., "Expression of cloned genes in *E. coli*" in Molecular Cloning: A laboratory manual (1989) Cold Spring Harbor Laboratory Press, New York, USA, 9.47–9.62 and 11.45–11.61.

More specifically, "stringent conditions" as used herein refer to hybridization in 6.0×SSC at about 45° C., followed by a wash of 2.0×SSC at 50° C. For selection of the stringency the salt concentration in the wash step can be selected, for example from about 2.0×SSC at 50° C., for low stringency, to about 0.2×SSC at 50° C., for high stringency. In addition, the temperature in the wash step can be increased from low stringency conditions at room temperatures, about 22° C., to high stringency conditions at about 65° C.

The term "isolated" as used throughout this application refers to a nucleic acid or polypeptide having an ISL activity and is substantially free of cellular material or culture medium, when produced by recombinant DNA techniques, or chemical precursors or other chemicals, when synthesized chemically. An isolated nucleic acid is preferably free of sequences which naturally flank the nucleic acid (i.e. sequences located at the 5' and the 3' ends of the nucleic acid) in the organism from which the nucleic acid is derived.

ISL can be isolated and purified from activated T cells by affinity chromatography using a monoclonal antibody against ISL. It is also preferred to use other known protein purification techniques, including immunoprecipitation, gel filtration, ion exchange chromatography, chromatofocussing, isoelectric focussing, selective precipitation, electrophoresis, and the like. Fraction isolated during purification procedures can be analyzed for the presence of ISL activity by using ISL specific antibodies.

The polypeptides according to the invention can also be produced by recombinant means, or synthetically. Non-glycosylated ISL polypeptide is obtained when it is produced recombinantly in prokaryotes. With the aid of the nucleic acid sequences provided by the invention it is possible to search for the ISL gene or its variants in genomes of any desired cells (e.g. apart from human cells, also in cells of other mammals), to identify these and to isolate the desired gene coding for the ISL protein. Such processes and suitable hybridization conditions are known to a person skilled in the art and are described, for example, by Sambrook, J., et al., "Expression of cloned genes in *E. coli*" in Molecular Cloning: A laboratory manual (1989) Cold Spring Harbor Laboratory Press, New York, USA, and B. D. Hames, S. G. Higgins, Nucleic acid hybridisation—a practical approach (1985) IRL Press, Oxford, England. In this case the standard protocols described in these publications are usually used for the experiments.

The use of recombinant DNA technology and the knowledge of the HIV inhibition assay enables the production of numerous active ISL derivatives. Such derivatives can, for example, be modified in individual or several amino acids by substitution, deletion or addition. The derivatization can, for example, be carried out by means of site directed mutagenesis. Such variations can be easily carried out by a person skilled in the art (J. Sambrook, B. D. Hames, loc. cit.). It merely has to be ensured by means of the above-mentioned HIV inhibition assay that the characteristic properties of ISL (inhibition of virus replication) are preserved. The invention therefore in addition concerns an ISL polypeptide which is a product of a prokaryotic or eukaryotic expression of an exogenous DNA.

The invention further concerns an isolated nucleic acid molecule which codes for a polypeptide or active fragment or derivative thereof, which inhibits the replication of HIV-1 in CD8+-depleted PBMC, said PBMC being prepared from buffy coat of non-retrovirally infected normal human blood samples, in the above-mentioned HIV inhibition assay, and wherein said nucleic acid molecule is selected from the group of i) a DNA molecule as shown in SEQ ID NO:1 or a sequence complementary to the sequence shown in SEQ ID NO:1, ii) nucleic acid molecules which hybridize with SEQ ID NO:1 or SEQ ID NO:3 or which hybridize with a DNA sequence complementary to SEQ ID NO:1 or SEQ ID NO:3, under stringent conditions, iii) nucleic acid molecules which, if there was no degeneracy of the genetic code, would hybridize under stringent conditions with the sequences defined in i) or ii), with the proviso that said isolated nucleic acid molecule is not identical with SEQ ID NO:3.

In a preferred embodiment of the invention, also nucleic acid molecules are disclaimed which code for a polypeptide of SEQ ID NO:4.

With the aid of such nucleic acids coding for an ISL protein, the protein according to the invention can be obtained in a reproducible manner and in large amounts. For expression in prokaryotic or eukaryotic organisms, such as prokaryotic host cells or eukaryotic host cells, the nucleic acid is integrated into suitable expression vectors, according to methods familiar to a person skilled in the art. Such an expression vector preferably contains a regulatable/ inducible promoter. These recombinant vectors are then introduced for the expression into suitable host cells such as, e.g., E. coli as a prokaryotic host cell or. Saccharomyces cerevisiae, Terato carcinoma cell line PA-1 sc 9117 (Büttner et al., Mol. Cell. Biol. 11 (1991) 3573–3583), insect cells, CHO or COS cells as eukaryotic host cells and the transformed or transduced host cells are cultured under conditions which allow an expression of the heterologous gene. The isolation of the protein can be carried out according to known methods from the host cell or from the culture supernatant of the host cell. Such methods are described for example by Ausubel I., Frederick M., Current Protocols in Mol. Biol. (1992), John Wiley and Sons, New York. Also in vitro reactivation of the protein may be necessary if it is not found in soluble form in the cell culture.

The detection of transformed or transduced host cells which recombinantly produce the ISL protein and the purification of the protein are preferably carried out by means of antibodies which bind to this protein. Such antibodies can be obtained in a simple manner according to known methods by using the protein according to the invention as an antigen or an immunogen.

The invention therefore in addition concerns the use of the protein with ISL activity according to the invention for the production of antibodies which bind to this protein.

Anti-ISL antibodies are produced by immunization and appropriate vertebrate host with purified ISL or polypeptide derivatives of ISL, preferably with an adjuvant. Said techniques are well-known in the literature and are described, for example, by Harlow and Lane eds., Antibodies: A laboratory manual (1988), Cold Spring Harbor Laboratories Press.

For this, animals which are usually used for this purpose, such as, in particular, sheep, rabbits or mice, are immunized with the protein according to the invention (preferably with the protein of FIG. 3), and subsequently the antiserum is isolated from the immunized animals according to known methods or spleen cells of the immunized animals are fused with immortalized cells, such as e.g. myeloma cells, according to the method of Köhler and Milstein (Nature 256 (1975) 495–497). Those cells which produce a monoclonal antibody against the ISL protein are selected from the hybridoma cells obtained in this way and cloned. The monoclonal or polyclonal antibodies obtained in this way can be bound to a support material, such as e.g. cellulose, for an immunoabsorptive purification of ISL. Furthermore, antibodies of this kind can be used for the detection of ISL in samples, such as e.g. cut tissue or body fluids, preferably for the determination of viral infections and virally induced benign and malignant diseases, most preferably for the determination of retroviral infections in mammalian samples. In such assays ISL is bound immunologically to its antibody in the specific step. The invention therefore additionally concerns specific antibodies against the ISL protein preferably the ISL proteins not disclosed by Cruikshank, which are obtainable by immunizing an animal with said ISL protein and isolating the antibodies from the serum or spleen cells of the immunized animals, and their use for the determination of ISL.

The invention in addition concerns the use of a polypeptide defined in the above-mentioned manner including a protein of SEQ ID NO:3, for the production of a pharmaceutical agent and for the treatment of viral infections, preferably retroviral infections such as HIV infections, and for use in therapy of benign and malignant diseases, especially in tumor therapy, most preferably for the treatment of viral-induced tumors.

The protein is processed, if desired together with the usually used auxiliary agents, fillers and/or additives, in a pharmaceutical formulation for the said therapeutic applications.

The invention therefore in addition concerns a therapeutic composition containing a ISL polypeptide according to the invention and if desired together with the auxiliary agents, fillers and/or additives that are usually used.

When the polypeptides according to the invention are applied for therapeutic use, their doses depend on the intended use. To find out the dose and optimize the application, usually such properties of the polypeptide as the half-life and bioavailability and the patient's age and weight will also be taken into account. Optimum therapeutic effectiveness is achieved when the polypeptides according to the invention are applied as soon alter the infection as possible, preferably as soon after the first virus peak as possible. Here it is important that a concentration of the polypeptides and substances according to the invention which effectively inhibits virus replication is retained in the blood during the early stage of viral infection. This can be accomplished, for example, by the application of 1 to 1000 μg/patient of the polypeptide according to the invention at 12 to 72 h-intervals. The period of application can be determined, suitably, by the method of determination of virus replication or virus quantity according to the invention or by other methods of virus determinations known to those skilled in the art. The application period may be in the range of from a few days to a few months.

The invention further concerns the use of the ISL genes or fragments thereof, preferably nucleic acid molecules coding for a polypeptide having ISL activity, or activating polynucleotides from the 5' untranslated region, in gene therapy, and in particular, for the production of medicaments for gene therapy, preferably for an antiviral or immunosuppressive therapy, or a therapy of benign or malignant diseases.

Gene therapy of somatic cells can be accomplished by using, e.g., retroviral vectors, other viral vectors, or by non-viral gene transfer (for clarity cf. T. Friedmann, Science 244 (1989) 1275; Morgan 1993, RAC DATA MANAGEMET REPORT, June 1993).

Vector systems suitable for gene therapy are, for instance, retroviruses (Mulligan, R. C. (1991) in Nobel Symposium 8: Ethiology of human disease at the DNA level (Lindsten, J. and Pattersun Editors) 143–189, Raven Press), adeno associated virus (McLughlin, J. Virol. 62 (1988), 1963), vaccinia virus (Moss et al., Ann. Rev. Immunol. 5 (1987) 305), bovine papilloma virus (Rasmussen et al., Methods Enzymol. 139 (1987) 642) or viruses from the group of the herpes viruses such as Epstein Barr virus (Margolskee et al., Mol. Cell. Biol. 8 (1988) 2937) or herpes simplex virus.

There are also known non-viral delivery systems. For this, usually "nude" nucleic acid, preferably DNA, is used, or nucleic acid together with an auxiliary agent, such as, e.g., transfer reagents (liposomes, dendromers, polylysine-transferrine-conjugates (Feigner et al., Proc. Natl. Acad. Sci. USA 84 (1987) 7413).

There is particularly preferred an ex vivo gene therapy as described, e.g., in W. F. Anderson et al., U.S. Pat. No. 5,399,346. According to this method a polypeptide according to the invention is provided to a human by introducing human cells into a human, said human cells having been treated in vitro to insert therein a DNA segment encoding a polypeptide according to the invention, said human cells expressing in vivo in said human a therapeutically effective amount of said polypeptide. As human cells there are used preferably fibroblasts or autologous hematopoietic stem cells which are characterized preferably by CD3+, CD4−, CD8−. Primitive human hematopoietic progenitor cells, which are characterized by a high expression of CD34 and the absence of CD38 expression, are particularly preferred. However, also more differentiated hematopoietic stem cells such as CD34+ and CD38+ cells can be used. Such cells are described, e.g., by Terstappen et al., Blood 77 (1991) 1218 or Huang and Terstappen, Nature 360 (1992) 745. For the transfection of fibroblasts it is preferred to use cytomegalovirus (CMV)-based vectors. For the transfection of hematopoietic stem cells it is preferred to use retroviral vectors based on the molony murine leukemia vector (MMLV). Such techniques are described in the state of the art, e.g., in the above-mentioned U.S. Pat. No. 5,399,346 which is incorporated herein by reference. For the regulation of the therapeutic application, the use of a suicide gene system (e.g., tk-Gen (Ganciclovir)) is preferred.

Another preferred method of gene therapy is based on homologous recombination. In this, either the gene coding for the ISL protein can be inserted in one or more copies into the genome of somatic cells and/or the ISL gene endogenously present in the cells can be modulated, preferably activated.

Methods of homologous recombination are described, e.g., in Kucherlapati, Proc. in Nucl. Acids Res. and Mol. Biol. 36 (1989) 301; Thomas et al., Cell 44 (1986) 419–428; Thomas and Capecchi, Cell 51 (1987) 503–512; Doetschman et al., Proc. Natl. Acad. Sci. USA 85 (1988) 8583–8587 and Doetschman et al., Nature 330 (1987) 576–578. In these methods, a portion of DNA to be integrated at a specific site in the genome (gene fragment of ISL) is bound to a targeting DNA. The targeting DNA is a DNA which is complementary, (homologous) to a region (preferably within or proximal to the ISL gene) of the genomic DNA. When two homologous portions of a single-stranded DNA (e.g. the targeting DNA and the genomic DNA) are in close proximity to one another they will hybridize and form a double-stranded helix. Then the ISL gene fragment and the targeting DNA can be integrated into the genome by means of occurrence of recombination. This homologous recombination can be carried out both in vitro and in vivo (in the patient).

Preferably, there is used a DNA which codes for a protein having ISL activity, a fragment which inhibits ISL expression (knock-out sequence) or a fragment capable of activating, after integration of the genome of a cell, expression, in this cell, of a protein having ISL activity. Such a fragment may be, for example, a promoter and/or enhancer region which is heterologous to the corresponding ISL region or which, after integration into the ISL gene, activates the actually silent or to a little extent expressed ISL gene transcriptionally and/or translationally.

Thus, by means of this DNA, one or more ISL genes are newly introduced into the target cell, or the essentially transcriptionally silent gene in the genome of a mammalian cell is activated in such fashion that the mammalian cell is enabled to produce endogenous ISL protein. To this end, a DNA construct is inserted into the genome by homologous recombination, the DNA construct comprising the following: a DNA regulatory element capable of stimulating expression of this gene if operatively linked thereto; and one or more DNA target segments which are homologous to a region in this genome, which region is within or proximal to this gene. This construct is inserted into the genome of the mammalian cell in such fashion that the regulatory segment is operatively linked to the gene which codes for the protein having ISL activity. Preferably, the construct further comprises amplifying sequences, especially if genes coding for proteins with ISL activity are inserted into the cell.

For the introduction of ISL genes into the target cells, the construct comprises a regulatory element, one or more ISL genes and one or more target segments. The target segments are chosen in such a way that they hybridize with an appropriate region of the genome, whereby, after homologous recombination, the inserted exogenous ISL genes are expressed.

There are known a large number of processes by which homologous recombination can be initiated. Preferably, homologous recombination takes place during DNA replication or mitosis of the cells. A DNA of this kind can be used for the production of an agent for therapeutic treatment of tumors and viral infection or for the production of homologous or heterologous ISL protein in a host organism.

A further subject-matter of the invention is a method for the determination of ISL polypeptides, nucleic acid sequences, virus-activated cells and ISL expression, preferably in samples of the human body such as human cell preparations, cell supernatants and body fluids such as blood, serum or plasma. Such a determination is useful for the detection of a viral infection, preferably of a mammalian, especially human, cell population. This method is particularly useful for the determination of the activation state of said cells and for the determination of a viral, preferably retroviral, infection of CD4+ cells. The diagnostic method is preferably applied immediately or as soon as possible after the first virus peak.

A further subject-matter of the invention is the use of an antibody which binds immunologically to a polypeptide which is obtainable by immunizing an animal with an ISL, polypeptide and isolating the antibodies from the serum or spleen cells of the immunized animals, for the determination of the ratio of activated/non-activated CD8+ and/or CD4+ cells in body fluids, especially in blood, serum or plasma.

Such tests can be provided on the basis of antibodies which are directed against part or all of ISL polypeptides. Such antibodies can be polyclonal or monoclonal antibodies, chimeric antibodies, humanized antibodies or fragments thereof such as F(ab), F(ab)$_2$, single chain F$_v$, or the like. In such an assay, the antibodies are used for immuno-specific recognition of ISL. The further detection (with and without separation of this complex, and subsequent monitoring) can be done by the immuno-assays which are widely known in the state of the art. For instance, the antibody can be labelled by a monitoring agent such as a fluorescence indicator, radio-active or enzymatic labelling.

There is particularly preferred a diagnostic determination of ISL concentrations in serum and other body fluids as well as the number of ISL-producing cells, e.g., for the detection of acute or chronic infections (e.g. even in blood donors) or for monitoring the course of ((retro)viral) infections (e.g. in patients suffering from AIDS), wherein antibodies that are provided with a fluorescent indicated or a radioactive or enzymatic label or with a labelled anti-antibody are reacted, brought into contact with ISL or ISL-producing cells, the antigen/antibody complexes are separated in a known manner and their concentration is determined via the label.

A suitable test method comprises the steps of incubating CD8+ T cells, in vitro, with the substance to be tested and determining ISL activity, preferably after 1 to 12 days, by detecting ISL expression according to the invention or by determining ISL polypeptide, preferably by means of an anti-ISL-antibody-based test. Such a test is carried out, for example, in the following manner:

a) commercially available 96-well ELISA plates are coated with monoclonal anti-ISL-antibodies;

b) the sample to be tested for ISL content is added to an antibody coated well for 1 h at room temperature and the well is washed;

c) bound ISL is detected by incubation of an affinity purified polyclonal Goat-anti-ISL-IgG-Preparation followed by an anti-Goat specific horse radish peroxidase labelled antibody and subsequent visualisation with OPD.

Other immunological assays based on the state of the art are also suitable.

It is also possible to provide a test on the basis of the nucleic acid sequences of the ISL protein provided by the invention which can be used to detect nucleic acids preferably RNAS, most preferably mRNAS which code for ISL proteins. Such a test can for example be carried out in cells or cell lysates and by means of nucleic acid diagnostics. In this case the sample to be examined is brought into contact with a probe which would hybridize with the nucleic acid sequence coding for the ISL protein. A hybridization between the probe and nucleic acids from the sample indicates the presence of expressed ISL proteins. Such methods are known to a person skilled in the art and are for example described in WO 89/06698, EP-A 0 200 362, U.S. Pat. No. 2,915,082, EP-A 0 063 879, EP-A0 173 251, EP-A 0 128 018. In a preferred embodiment of the invention, the nucleic acid of the sample which codes for an ISL protein is amplified before testing, e.g. by the well-known PCR technique. A derivatized (labelled) nucleic acid probe is usually used in the field of nucleic acid diagnostics. This probe is brought into contact with a carrier-bound denatured DNA or RNA from the sample and in this process the temperature, ionic strength, pH value and other buffer conditions are selected in such a way that—depending on the length of the nucleic acid sample and the resulting melting temperature of the expected hybrid—the labelled DNA or RNA can bind to homologous DNA or RNA (hybridization, see also Southern, E. M., J. Mol. Biol. 98 (1975), 503–517; Wahl, G. M. et al., Proc. Natl. Acad. Sci. USA 76 (1979), 3683–3687). Suitable carriers are membranes or carrier materials based on nitrocellulose (e.g. Schleicher and Schüll, BA 85, Amersham Hybond, C.), reinforced or bound nitrocellulose in a powder form or nylon membranes derivatized with various functional groups (e.g. nitro group) (e.g. Schleicher and Schüll, Nytran; NEN, Gene Screen; Amersham Hybond M.; Pall Biodyne).

The hybridized DNA or RNA is then detected by incubating the carrier, after thorough washing and saturation to prevent unspecific binding, with an antibody or antibody fragment. The antibody or antibody fragment is directed towards the substance incorporated into the nucleic acid probe during the derivatization. The antibody is in turn labelled. It is, however, also possible to use a directly labelled DNA. After incubation with the antibodies, it is washed again in order to only detect specifically bound antibody conjugates. The determination is then carried out via the label of the antibody or antibody fragment according to well-known methods.

The detection of the ISL expression can be carried out, for example as an in situ hybridization with immobilized whole cells using immobilized tissue smears and isolated metaphase chromosomes, as a colony hybridization (cells) and plaque hybridization (phages and viruses), as a Northern hybridization (RNA detection), as serum analysis (e.g. cell type analysis of cells in serum by slot-blot analysis), after amplification (e.g. PCR technique).

The invention therefore includes a method for the detection of nucleic acids which code for an ISL protein which is characterized in that the sample to be examined is incubated with a nucleic acid probe which is selected from the group comprising a) the DNA sequences shown in SEQ ID NO:1 and SEQ ID NO:3 or a complementary sequence to these, b) nucleic acids which hybridize under stringent conditions with one of the sequences from a), the nucleic acid probe is incubated with the nucleic acid from the sample and the hybridization of the nucleic acid in the sample and nucleic acid probe is detected, if desired, via a further binding partner.

Thus, ISL is a valuable prognostic marker in viral, benign and malignant disease diagnostics.

Surprisingly, it was found that according to the invention it is not necessary to use an ISL polypeptide or nucleic acid directly for inhibition of the replication of viruses. It is also possible to use substances which induce production of ISL in cells. Such cells preferably are human blood lymphocytes, especially $CD8^+$ cells. For induction of ISL production said cells are incubated, in vivo or in vitro, with such activating substances. If activation is performed in vitro the cells are subsequently administered to the patient, e.g., according to the above-mentioned U.S. Pat. No. 5,399,346. According to the invention it is easily possible to identify such substances which activate ISL production.

It has been found that such substances are, e.g., phytohaemagglutinin (PHA), Concanavalin A (ConA), histamine, polypeptides or nucleic acid molecules. Nucleic acid molecules are used as vectors which contain further elements securing expression of said nucleic acid molecules in the target cells. Said elements are known in the state of the art (e.g., regulatory sequences, promoter and/or operator regions). Suitable target cells for transfection with such nucleic acid molecules are preferably human cells, most preferably human blood cells such as lymphocytes, especially $CD8^+$ cells.

Therefore, a further subject-matter of the invention is a method for the identification and production of a substance and a therapeutic agent for inhibition of the replication of viruses in a patient. Said method comprises combining with a pharmaceutically acceptable carrier a therapeutically effective amount of a substance which activates expression of a protein with ISL activity in $CD8^+$ cells preferably in vivo. The protein the expression of which is activated is preferably a protein with the amino acid sequence shown in SEQ ID NO:2. A suitable substance can be identified in an assay (substance assay) wherein a) PBMC from healthy blood donors are isolated by Ficoll-gradient separation;

b) $CD8^+$ cells are isolated by magnetic cell sorting;

c) the purity of the preparation is tested by FACS analysis;

d) the preparation should have a content of approximately 95% $CD8^+$ cells and 5% non-$CD8^+$ contaminants to ensure adequate stimulation of $CD8^+$ cells;

e) the substance to be tested for induction of expression of ISL activity is added to the cell culture in a concentration range of 1 pM to 10 mM;

i) IL-2 is added to the cell culture (180 U/ml cell culture medium) or to the culture of the transfected cells if the substance is a nucleic acid molecule;

g) after three days medium is completely removed and cells are cultured with IL-2 (180 U/ml cell culture medium) for three days;

h) cell culture supernatant is centrifuged (×1000) to remove cells, sterile filtered, and aliquoted;

and further investigated in the above-mentioned HIV inhibition assay, whereby i) CD8$^+$-depleted PBMC are incubated with 50 µl of said cell culture supernatants/1.5×10$^6$ cells in 150 µl medium for half a hour at 37° C.;

k) said CD8$^+$-depleted PBMC are subsequently infected with HIV-1, preferably with HIV-1$_{SF2}$, by incubating 1.5×10$^6$ cells in 150 µl with 50 µl HIV-1 stock solution containing 50 tissue infectious doses 50 (TCID$_{50}$) for 1 h at 37° C.;

l) said infected CD8$^+$-depleted PBMC are washed to remove unbound HIV-1;

m) CD8$^+$-depleted PBMC are cultivated at 37° C. in a 5% CO$_2$ atmosphere and medium and said cell culture supernatant is replaced after 3, 6, 9, and 12 days;

n) the amount of HIV-1 in the CD8$^+$-depleted PBMC cell culture supernatants is determined at days 9 and 12 post infection by serially threefold dilutions of supernatant and inoculation in quadruplicate wells onto 2000 cells in 150 µl medium of a highly susceptible indicator cell line, which must be routinely infectable to an extent of 85% or greater with said HIV-1 strains, e.g. the human HTLV-transformed lymphoma cell line MT4;

o) virus replication in each well is determined 8 days post infection by determination of the reverse transcriptase (RT) in the cell culture supernatant (reverse Transcriptase Assay, Boehringer Mannheim GmbH, Biochemica, 68298 Mannheim, Germany, Order No.: 1468 120) of every single well following the instructions of the manufacturer;

p) the tissue culture infectious doses 50 (TCID$_{50}$) of the CD8$^+$-depleted PBMC cultures is calculated following the method published by Karber (Karber, G. 1931. Assay for statistical analysis of pharmacological experiments. Arch. Exper. Path. V. Pharmakol. 162, 148 according to the formula:

$$\log TCID_{50} = L - d(s - 0.5),$$

wherein

L=log of the lowest virus dilution d=log of virus dilution s=sum of virus-positive cell cultures;

q) inhibition of HIV-1 replication in the CD8$^+$-depleted PBMC cultures is calculated by comparison of virus content of cell culture supernatants in an assay according to steps i) to p) and the virus content of an assay according to steps i) to p) where the cell culture supernatant to be tested for inhibition of HIV replication is replaced by normal medium (untreated control);

r) inhibition is found if the amount of viral replication in CD8$^+$-depleted PBMC is inhibited in such a way that the amount of virus is only about 50%, more preferably 10%, most preferably 1% or less in comparison to the untreated control.

A further subject-matter of the invention is a therapeutic composition useful in treating a pathological condition characterized by excessive viral replication, especially retroviral replication, comprising at least a substance which activates ISL activity in CD8$^+$ T cells, and which is characterized by the properties of the above-mentioned substance assay and HIV inhibition assay, and a pharmaceutically acceptable carrier.

Such a substance, which is obtainable and characterized by the above-mentioned substance assay, is useful for the induction and/or activation of ISL in mammalian cells, for the inhibition of the replication of viruses, preferably retroviruses, especially HIV and/or HTLV, for therapeutic treatment of benign and malignant diseases and viral, preferably retroviral, especially HIV and/or HTLV, infections.

It is also particularly preferred to use said substances for therapeutic treatment of such viral infections as soon as possible after the infection, preferably as soon as possible after the first virus peak.

The following examples, sequence listing, and figures are provided to aid the understanding of the present invention, the true scope of which is set forth in the appended claims. It is understood that modifications can be made in the procedures set forth without departing from the spirit of the invention.

| Sequence listing | |
|---|---|
| SEQ ID NO:1 | represents the nucleotide of ISL$_{agm}$ (African green monkey) and protein sequence derived therefrom. |
| SEQ ID NO:2 | represents the protein sequence of ISL$_{agm}$. |
| SEQ ID NO:3 | represents the nucleotide of LCF and protein sequence derived therefrom. |
| SEQ ID NO:4 | represents the protein sequence of LCF. |
| SEQ ID NO:5 | represents Primer 1 for ISL cloning. |
| SEQ ID NO:6 | represents Primer 2 for ISL cloning. |
| SEQ ID NO:7 | represents the DNA sequence of HIV-1$_{SF2}$. |
| SEQ ID NO:8 | represents the DNA sequence of HIV-1$_{SF33}$. |

LEGENDS TO THE FIGURES

FIG. 1: Inhibition of the HIV-1$_{SF2}$ replication on the T cell lymphoma line H9 by purified recombinant ISL (B) and by a cell culture supernatant of activated human CD8$^+$ lymphocytes (ISL) (C). A quantitative comparable inhibition of viral replication was measured using the following HIV and SIV strains: HIV-1$_{SF2}$, HIV-1$_{SF33}$, HIV-1$_{SF162}$, HIV-2$_{UC3}$ and SIV$_{agm}$. ((A) comparison, only tissue culture).

Figure 2:
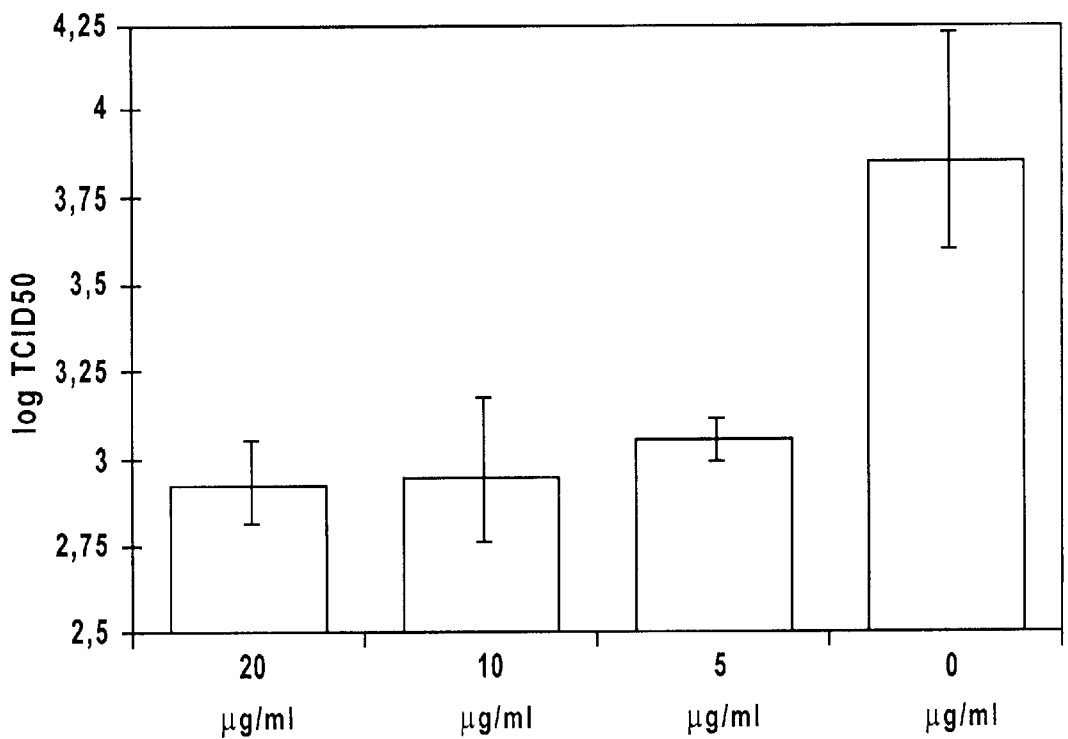

FIG. 2: Inhibition of HIV-1$_{SF2}$ replication on primary CD4$^+$ lymphocytes by recombinant ISL. Log TCID$_{50}$: logarithm of tissue culture infectious dose$_{50}$ (infectious dose$_{50}$ of cell culture). Quantitatively comparable inhibitions are seen with the following immunodeficiency virus strains: HIV-1$_{SF33}$, HIV-1$_{SF162}$, HIV-2$_{UC3}$ and SfV$_{agm}$.

FIG. 3: Comparison of DNA and polypeptide sequences of human and monkey ISL.

a) human; b) *P. troglodytes* (chimpanzee); c) *M. mulatta* chin., d) *M. mulatta* ind.; e) *M. nemestrina*; f) *M. fascicularis*; g) *C. aethiops* (AGM).

EXAMPLE 1

Cloning, Expression and Purification of ISL 1.1 RNA Isolation

5×10$^7$ PBMC (human or monkey) were cultured for 48 hours with 10 µg/nd concanavalin A and 180 units/ml IL-2. In order to prepare the RNA, the cells were washed once with PBS and subsequently lysed with 5 ml denaturing solution (RNA isolation kit, Stratagene). After addition of 1 ml Na acetate, 5 ml phenol and 1 ml cloroform/isoamyl alcohol (24:1), the lysate was kept on ice for 15 minutes. The aqueous phase was subsequently admixed with 6 ml isopropanol in order to precipitate the RNA and stored for 2 hours at −20° C. The precipitate was finally washed once with absolute ethanol and dissolved in 150 μl H$_2$O. The yield was determined photometrically and was 120 μg.

1.2 cDNA Synthesis

The mixture for cDNA synthesis contained 10 μg RNA, 0.2 μg oligo-dT, 13 mM DTT and 5 μl bulk first-strand reaction mix (first-strand cDNA synthesis kit, Pharmacia) in a volume of 15 μl. The reaction was incubated for 1 hour at 37° C. and subsequently stored at −20° C. for later use.

1.3 Amplification and Cloning of ISL cDNA

For the amplification of ISL cDNA by means of PCR and for the following cloning, the following oligonucleotides were synthesized:

Primer 1: GCTGCCTCTCATATGGACCTCAACTC-CTCCACTGACTCT (SEQ ID NO:5)
Primer 2: GATGGACAGGGATCCCTAGGAGTCTC-CAGCAGCTGTGG (SEQ ID NO:6)

The primers introduce additional NdeI or BamHI cleavage sites.

The PCR mixtures (100 μl reaction volumes) each contained 1 μl cDNA (from the synthesis in section 3), 50 pmol primer 1 and 2, 12.5 μmol dNTPs, 10 μl 10×TAQ buffer and 2.5 units Taq polymerase (Perkin-Elmer). The cycle conditions were 30 sec, 94° C., 1 min, 53° C. and 1 min, 72° C. 35 cycles were carried out.

The PCR products were purified and digested for 16 hours at 37° C. with NdeI and BamHI. For the cloning preparation the vector pET15b (Novagen) was also cleaved with NdeI and BamHI and subsequently purified over an agarose gel.

The ligations were carried out for 2 hours at room temperature in 20 μl mixtures containing 100 ng vector, 25 ng PCR product (Insert), 2 μl 10×ligase buffer and 0.2 μl ligase (New England Biolabs). After transformation by electroporation at 2.5 kvolt, 25 μfarad, 200 ohm (BIO-RAD electroporator) in E. coli DH5, the cells were placed on ampicillin-resistant plates.

Recombinant clones were identified by restriction analysis of plasmid preparations (pMISLB) and transformed into the strain BL21-DE3 for the intended protein expression. The cloning of ISL cDNA could be additionally confirmed by determining the nucleotide sequences. The sequences found agreed with the published LCF sequence (Cruikshank et al in Proc. Natl. Acad. Sci. USA, Vol. 91 (1994) 5109–5113) apart from a discrepancy in codon 96. In contrast to the published sequence codon 96 is not composed of the base sequence TTG but rather of the sequence TTT and thus codes for leucin and not for phenylalanine. The sequencing of further ISL clones which were derived from independent PCR amplifications clearly showed that the authentic ISL sequence in codon 96 is indeed represented by the sequence TTT.

Proteins homologous to ISL are isolated in an analogous manner from body fluids containing CD8$^+$ lymphocytes from animals infected with immunodeficiency virus and in particular from those which are infected without falling ill such as chimpanzees (P. troglodytes), African green monkeys (C. aethiops), sooty mangabees, M. mulatta chin., M. mulatta ind., M. nemestrina or M. fascicularis. It is possible to use these proteins and nucleic acids therapeutically and in diagnostics in a similar manner to human ISL.

EXAMPLE 2

Expression and Purification of Recombinant, Soluble ISL 2.1 Human ISL

ISL is expressed aminoterminally in a fusion with a leader of 6 histidine residues in the vector pET15b. 20 ml overnight culture of pMISLB was used in each case to inoculate 2 liters of 2×TY/ampicillin medium. The cultures were shaken at 25° C. and when an OD$_{600}$ of 0.4 had been reached they were induced by addition of 1 ml 1M isopropyl-β-D-thiogalactoside. After a further 4 hours the bacteria were pelleted and frozen for 14 hours at −70° C.

The pellets were subsequently thawed and washed once with 250 ml PBS. The cells were lysed in 50 ml ice-cold PBS by adjusting the suspension to 1% NP-40, 10 mM EDTA, 0.4 M NaCl and 50 μg/ml lysozyme. After 60 minutes incubation on ice the lysate was freed from insoluble components by centrifugation.

The ISL with 6 histidine residues at the amino terminus (His6-ISL) was purified by means of a chromatographic step. For this the lysate was adjusted to 20 mM MgCl$_2$, 10 mM imidazole, 0.5 M NaCl and applied to a Ni$^{2+}$-NTA-Agarose (Qiagen) column with a flow rate of 0.1 ml/min. 0.25 ml Ni$^{2+}$-NTA-Agarose was used per liter initial culture. The column was subsequently washed with 20 volumes PBS, 25 mM imidazole and the His6-ISL was finally eluted with 4 ml PBS, 200 mM imidazole.

His6-ISL fusion protein isolated in this manner had a degree of purity of over 90% after testing in SDS gel electrophoresis. The yields were ca. 5 mg protein per liter initial culture. The purified protein was finally freed from lower molecular impurities such as e.g. imidazole by gel filtration over NAP-10 columns (Pharmacia) and transferred to PBS. Afterwards the protein concentrations were 0.5–1 mg/ml. (Purification scheme see Table 1).

TABLE 1

Flow diagram of the purification of ISL

E. coli culture B121-DE3 transfoumed using pMISL-1huB
↓
induce with 1 mM IPTG
↓
lyse the cells (NP-40, EDTA, lysozyme)
↓
adjust to 20 mM MgCl$_2$
10 mM imidazole, 0.5M NaCl
bind to Ni$^{2+}$-NTA-Agarose
wash with 25 mM imidazole/PBS
↓
elute with 200 mM imidazole/PBS
↓
re-buffer in PBS
↓
check the purity by SDS-PAGE
↓
protein determination 2.2 ISL Derivative LCF Since LCF has an almost homologous sequence, LCF was specifically cloned from a cDNA library of activated human CD8$^+$ lymphocytes, in addition to an experiment on ISL cloning, in order to examine the former for a possible anti-viral efficacy. It could be shown that LCF has an ISL action and is papable of inhibiting HIV as well as SIV replication.

2.3 ISL Derivative From African Green Monkey (ISL-agm)

A protein homologous to human ISL (SEQ ID NO:1) can be isolated from African green monkey (ISL-agm). The nucleotide sequences of human ISL (ISL-hu (SEQ HD NO:2)) differ as shown in the tables below:

TABLE 2a

Comparison of ISL-hu and ISL-agm DNA sequences

| Nucleotide | 19 | 72 | 73 | 92 | 117 | 156 | 159 | 162 | 226 | 257 | 312 | 339 | 342 | 348 | 360 | 361 | 383 |
|---|---|---|---|---|---|---|---|---|---|---|---|---|---|---|---|---|---|
| ISL-hu | T | T | A | G | G | T | A | C | G | G | A | C | C | A | G | T | G |
| ISL-agm | A | C | T | A | T | C | G | T | A | C | C | A | T | G | A | C | C |

TABLE 2b

Comparison of ISL-hu and ISL-agm protein sequences

| Amino acid | 7 | 25 | 31 | 76 | 86 | 121 | 128 |
|---|---|---|---|---|---|---|---|
| ISL-hu | S | T | C | V | G | S | G |
| ISL-agm | T | S | Y | I | A | P | A |

2.4 ISL Derivatives From Other Monkeys

Nucleic acid and protein sequences of ISL from other monkeys can be isolated in the same manner. A sequence comparison is shown in FIG. 3.

2.5 Recombinant Expression of Fusion-free ISL in E. coli

The DNA sequence coding for ISL is modified in such fashion as to allow for efficient expression in E. coli.

For expression, an expression plasmid is transfected into a suitable E. coli strain. Such strains are, in the case of the use of an expression plasmid under the control of lac repressor such as the expression plasmid p11379, strains which possess a sufficiently high intracellular concentration of lac repressor. These kinds of strains can be prepared by transfection of a second plasmid such as pREP4 (Diagen GmbH), pUBS 500 or pUBS520 (Brinckmann et al., Gene 85 (1989) 109–114). The applied E. coli strains should preferably have a low protease activity of the cells proper, as is the case, for instance, with E. coli UT5600 (Earhart et al., FEMS Microbiology Letters 6 (1979) 277–280), E. coli BL21 (Grodberg and Dunn, J. Bacteriol. 170 (1988) 1245–1253) or E. coli B. Then, expression cultivation is accomplished in a fashion according to the state of the art, as a protein aggregate, and processed according to the procedures described in EP 0 241 022, EP 0 364 926, EP 0 219 874 and DE-A 40 37 196.

In detail, for example, the following procedure is applied for this purpose: ISL-containing lysates from E. coli fermentations were adjusted to 6 M guanidinium hydrochloride, 100 mM TrisHCl at pH 8, 1 mM EDTA, subsequently adjusted to a pH of 3 to 4 and dialyzed against 4 M guanidinium hydrochloride at pH 3.5. The renaturing of the solubilized protein is then carried out in 1 M arginine at pH 8, 1 mM EDTA, 5 mM GSH (glutathione, reduced) and 0.5 mM GSSG (glutathione, oxidized). ISL can be further purified by usual chromatographic techniques.

2.6 Recombinant Expression of ISL in Mammalian Cells

For this, the cDNA is ligated into a vector in which it is transcribed into mammalian cells, preferably CHO or COS cells, on the basis of a strong promoter-enhancer system. Such promoters and enhancers are mostly from viruses such as SV40, hCMV, polyoma or retroviruses. As an alternative there can also be applied promoter-enhancer systems which are specific to a certain cell type or tissue type, such as, for instance, WAP-, MMTV- or immune globuline promoter, or systems which are inducible, such as, for instance, metallothioneine promoter. This kind of vector supplements the ISL cDNA (if the latter is used) with donor and acceptor signals for RNA processing as well as a signal for poly-A-addition. For example, pCMX-pL1 (Umesono et al., Cell 65 (1991) 1255–1266) is such a suitable vector. Into the one and only EcoRI cleavage site of this vector the cDNA provided with EcoRI linkers is ligated, wherein it is ensured by restriction analysis with the aid of the other cleavage sites in the polylinker of this vector that the cDNA is oriented in reading direction of the CMV promoter. An absolutely analogous procedure is applied when cloning into other vectors, e.g. into pCDNA3 (Invitrogen, San Diego/USA) or pSG5 (Stratagene, Lajolla/USA). The DNA of the so obtained expression plasmids is prepared from *E. coli* and transfected into the mammalian cells, applying techniques that are specific to the cell types in the particular case (Methods of Enzymology 185 (Goeddel, David V., (ed.), Gene Expression Technology, Academic Press 1991, section V). After transfection, the cells are cultured in MEM (Gibco) without addition of fetal calf serum, whereby ISL is detectable in the cell culture supernatant after 48 hours.

EXAMPLE 3

Testing the Inhibition of HIV Replication by ISL on T Cell Lymphoma Lines, Primary Lymphocytes (PBMC) and Purified Primary CD4$^+$ Lymphocytes 3.1 Obtaining HIV Virus Stocks for Infecting the Cells The human immunodeficiency viruses (HIV-1, HIV-2) and the simian immunodeficiency viruses (SIV) replicate in human T cell lymphoma lines as well as in primary CD4$^+$ lymphocytes. Cell culture supernatants containing viruses that are obtained from primary lymphocyte cultures (PBMC) usually contain more infectious viruses than those that are obtained from T cell lines. In the case of the HIV 1 strain HIV-$1_{SF162}$ replication is only possible on PBMC since this virus does not replicate in any of the known T cell lymphoma lines. The standard virus supernatants used in all the following experiments was therefore produced on primary lymphocytes. For this PBMC purified by means of a Ficoll gradient and stimulated with phytohaemagglutinin (PHA) (for a detailed description of the method see below) were infected with the HIV-1 strains HIV-$1_{SF2}$, HIV-$1_{SF33}$, HIV-$1SF_{162}$ (Cheng-Mayer, C., et al, J. Virol. 64 (1990) 4390–4398) and the HIV-2 strain HIV-$2_{UC3}$ (Castro, B. A., et al, Virology 178 (1990) 527–534). These viral strains were also passaged earlier exclusively on PBMC and the cell culture supernatants containing viruses were stored at −70° C.

For the infection 120×10$^6$ PBMC with a multiplicity of infection (MOI) of 0.1 were incubated for 2 hours at 37° C., the cells were washed with RPMI medium and cultured for 12 days in 40 ml cell culture medium (RPMI 1640, 20% FCS, 2 mM glutamine, 180 U/ml IL-2) corresponding to a cell count of 3×10$^6$/ml cell culture medium. The cell culture medium was changed on the third day upon which the cell count was again adjusted to 3×10$^6$/ml medium. On days 6, 9 and 12 the cell culture supernatant was collected, cells and cell debris were removed by centrifugation, it was sterilized by filtration (0.45 μm pore size) and stored in 0.5 ml aliquots at −70° C.

3.2 Cell Culture Conditions for the Propagation of T Cell Lymphoma Lines

The T cell lymphoma lines H9, CEM, Molt 4 clone 8, MT4 and C8166 are cultured at 37° C. and 5% $CO_2$ atmosphere in RPMI 1640 medium, supplemented with 10% FCS and 2 mM glutamine. The cells are passaged every third day while changing the medium at the same time and the cell count is adjusted to $1\times10^5$/ml.

3.3 Preparation and Propagation of Primary Blood Lymphocytes (PBMC)

Peripheral blood lymphocytes are prepared from "buffy coats" which have been isolated from normal blood donors. Whole blood is used to prepare PBMC from non-human primates such as African green monkeys and rhesus monkeys. For this the "buffy coat" or the whole blood is layered on a Ficoll-Hypaque gradient and centrifuged for half an hour at 1000×g. The serum supernatant is discarded, the mononuclear cells are collected and washed several times in Hanks medium. The cells ($3\times10^6$/ml) are taken up in RPMI 1640, 20% FCS, 2 mM glutamine and stimulated for three days with 9 μg/ml phytohaemagglutinin (PHA) and proliferated with 180 U/ml IL-2. The cells are cultured at 37° C. and 5% $CO_2$ atmosphere. Then the medium is completely changed and the cells are cultured further without PHA at a cell count of $3\times10^6$/ml culture medium or used in experiments.

3.4 Purifying the CD4+ and CD8+ Lymphocytes by Means of Magnetic Activated Cell Sorting (MACS)

The lymphocytes isolated by means of Ficoll gradients from a "buffy coat" are resuspended in 500 μl PBS-azide/$1\times10^8$ cells (phosphate buffered saline without $Ca^{2+}$ and $Mg^{2+}$, 0.01% sodium azide, 5 mM EDTA, pH 7.2). After addition of 20 ml CD8 microbeads/$1\times10^7$ expected cells (mouse anti-human CD8 antibodies, conjugated with magnetic particles, Miltenyi Biotec GmbH) they are incubated for 15 min at 4° C. 2 mg DTAF/$1\times10^7$ expected cells (anti-mouse IgG, FITC conjugated, Dianova Company) is added for a further 5 minutes at 4° C. After dilution with 25 ml PBS-azide/1% BSA it is again centrifuged (10 min, 1200 rpm, 4° C.). The supernatant is discarded, the cells are resuspended in 2 ml PBS/1% BSA and the cell suspension is applied to a column which is located in a magnetic separator (Miltenyi Biotec GmbH). CD8+ cells to which the CD8 microbeads are coupled are retained in the column, the flow fraction therefore contains all lymphocytes (ca. 80% CD4+ cells) except the CD8+ cells. After washing the column it is taken out of the holder and the CD8+ cell fraction is eluted with PBS-azide/1% BSA. The flow fraction and the CD8+ cell fraction are centrifuged, resuspended in cell culture medium (RPMI 1640, 20% FCS, 2 mM glutamine, 180 U/ml IL-2), the cell count is adjusted to $3\times10^6$ cells/ml and the cells are stimulated with PHA (9 mg/ml). The quality of the separation of the lymphocyte subpopulation is checked by means of FACS.

3.5 Titration of the HIV Virus Stock on Various Host Cells

PBMC, CD4+ lymphocytes and the T cell lymphoma lines H9 (Popovic, M., et al, Science 224 (1984) 497–500), Molt 4 clone 8 (Kikukawa, R. et al, J. Virol. 57 (1986) 1159–1162), C8166, MT4 and CEM (obtained from the American Type Culture Collection) were used as host cells. The titrations are carried out in 96-well plates.

a) Titration on PBMC and CD4+ Lymphocytes

The virus stocks HIV-1$_{SF2}$, HIV-1$_{SF33}$, HIV-1$_{SF162}$ (Cheng-Mayer, C., Quiroga, M., Tung, J. W., Dina, D. & Levy, J. A. (1990) HIV2$_{UC3}$ and SIV$_{agm}$ (Kraus, G., et al, Proc. Natl. Acad. Sci. USA 86 (1989) 2892–2896; Baier, M., et al, J. Virol. 63 (1989) 5119–5123) are diluted in three steps and 50 μl of each is pipetted into four independent PBMC or CD4+ lymphocyte cultures ($1\times10^6$ PBMC or CD4+ lymphocytes in each case) in 100 μl culture medium and incubated for one hour at 37° C. Viruses that are not cell bound are then removed by washing the cells with culture medium. Medium is changed (removal and addition of 100 μl medium each time) 3, 6, 9 and 12 days after infection. The cell culture supernatants of each individual culture from days 6, 9 and 12 are tested for their virus content by either carrying out a) a test for reverse transcriptase (according to the instructions of the test manufacturer Boehringer Mannheim GmbH, Germany)

b) a p24antigen ELISA (according to the instructions of the test manufacturer "Abbott") or c) infections of highly susceptible indicator cell lines (Ennen, J., et al, Proc. Natl. Acad. Sci. USA 91 (1994) 7207–7211).

b) Titration on T Cell Lymphoma Lines H9, CEM, Molt4/8

The virus stocks are diluted in three steps and 50 μl of each is pipetted into independent cell cultures (in each case $5\times10^4$ cells in 100 μl culture medium in U-well 96 cell culture plates) and incubated for I hour at 37° C. Washing and testing for infection is carried out according to the method described in 2a). The smaller initial cell count compared to PBMC cultures is due to the proliferative competence of the T cell lymphoma lines that during the course of the titration test grow to the critical cell density in the allotted cell culture volume of the microtiter plates of maximally 250 μl.

c) Titration of the T Cell Lymphoma Lines C8166 and MT4

The T cell lymphoma lines C8166 and MT4 are titrated according to the method described in 2b). The virus test is, however, not carried out using the above-mentioned test systems but the cell cultures are evaluated by light microscopy. In the case of infection by the viral strains HIV-1$_{SF2}$, HIV-1$_{SF33}$ and HIV-2$_{UC3}$ the C8166 and MT4 cells are killed by proliferation of the viruses which can be easily and rapidly identified using a microscope.

3.6 Calculation of the Tissue Culture Infectious Dose 50 ($TCID_{50}$)

$TCID_{50}$ is calculated according to the method published by Karber (Karber, G. 1931. Assay for statistical analysis of pharmacological experiments. Arch. Exper. Path. V. Pharmakol. 162, 148) according to the formula.

$$\log TCID_{50} = L - d(s - 0.5),$$

wherein

L=log of the lowest virus dilution d=log of virus dilution s=sum of virus-positive cell cultures

3.7 Testing Inhibition of HIV Replication by ISL

The effectiveness of ISL on HIV replication is tested on T cell lymphoma lines as well as on primary lymphocytes. The experiments start with toxicity and dose-finding experiments, in the further course one works with a non-toxic but maximally effective ISL concentration. These tests are carried out separately in 96-well microtitre plates in quadruplicates for each T cell line and PBMC as well as on total PBMC and also on CD4+ lymphocytes.

a) Dose-finding and Toxicity Experiments Using ISL on T Cell Lines $5\times10^4$ cells were incubated for 10 minutes at room temperature with various dilutions (40 μg/ml to 0.15 μg/ml) of ISL. The cells were then infected with the virus stocks mentioned under 1. They were infected in each case for one hour at 37° C. and 5% $CO_2$ atmosphere with 50 $TCID_{50}$ which was determined and calculated separately for each cell line (see above under 2.). Non-bound virus was removed by washing the cells with culture medium. The cells were resuspended in cell culture medium and the ISL concentration was adjusted to the initial concentration. In some experiments ISL was added again every day so as to ensure that the ISL concentration remained relatively constant. The medium was changed on days 3, 6, 9 and 12 after infection in the process of which the cell culture supernatants from days 6, 9 and 12 were examined quantitatively for their virus content using the test systems described supra. Parallel to this growth curves of the cultures were plotted (counting cells dyed with trypan-blue by means of light microscopy) which gave insight on the toxicity of ISL.

b) Dose-finding and Toxicity Experiments Using ISL on Primary PBMC

The experiments were carried out using total PBMC as well as purified CD4+ lymphocytes. $1 \times 10^6$ cells were incubated with ISL under the conditions described supra, infected with HIV and the cell culture supernatants were quantitatively examined for their virus content on days 6, 9 and 12 after infection. The toxicity of ISL on PBMC was determined with the aid of trypan blue staining and counting the cells by light microscopy.

c) Tests on the Mechanism of Action of ISL

It was examined whether ISL develops its inhibitory effect at the level of de-novo infection or during persisting HIV replication. Experiments were carried out for this in which the fully effective dose of ISL in the cell culture was present only during the one hour infection period. Parallel to this a constant ISL concentration was additionally maintained in the cell culture medium during the whole test period in another experimental mixture. This experiment allows a decision whether ISL inhibits the HIV infection or HIV replication or whether it is effective at both levels (FIGS. 1 and 2).

EXAMPLE 4

Qualitative and Quantitative Detection of ISL in Body Fluids and Cell Culture Supernatants ISL was detected by means of a modified enzyme linked immunosorbent assay (ELISA). For this monoclonal antibodies against ISL are prepared. These are absorbed onto the wells of an ELISA plate. The liquid to be tested for its ISL content is incubated, the monoclonal antibodies specifically react with ISL which is immobilized. Bound ISL is detected by means of an affinity-purified polyclonal anti-ISL antibody (obtained by immunizing a goat with ISL) which itself is made visible by means of a colour reaction using an anti-goat antibody coupled to peroxidase.

EXAMPLE 5

Direct Detection of Cells Producing ISL

The monoclonal antibody against ISL described above is used for the direct detection of cells producing ISL either for diagnostic purposes in the case of cells from patients or for cells in tissue culture. For this the cells are fixed with methanol while at the same time disrupting the cell membrane and incubated with the monoclonal anti-ISL antibody labelled with fluorescein isothiocyanate (FITC). It is evaluated with the aid of a fluorescence activated cell sorter (FACS).

LIST OF REFERENCES

Ausubel I., Frederick M., Current Protocols in Mol. Biol. (1992), John Wiley and Sons, New York Baier, M., et al, J. Virol. 63 (1989) 5119–5123
Blackbourn et al, Journal of Medical Primatology No. 23 (1994) 343–354
Brinckmann et al, Gene 85 (1989) 109–114
Büttner et al, Mol. Cell. Biol. 11 (1991) 3573–3583
Castro, B. A, et al, Virology 178 (1990) 527–534
Castro, Walker et al, Cellular Immunology 132 (1991) 246–255
Center, D. M., et al., J. Lab. Clin. Med. 125 (1995) 167–171
Chen et al, AIDS Research and Human Retroviruses Vol. 9, No. 11, 1079–1086
Cheng-Mayer, C., et al, J. Virol. 64 (1990) 4390–4398
Cheng-Mayer, C., et al, Virol. 65 (1991) 6931–6941
Cheng-Mayer, C., et at, Virol. 181 (1991) 288–294
Cruikshank and Center, Journal of Immunology 128 (1982) 2569–2574
Cruikshank et al, Journal of Immunology 138 (1987) 3817–3823
Cruikshank et al, Journal of Immunology 146 (1991) 2928–2934
Cruikshank et al, Proc. Natl. Acad. Sci. USA, Vol. 91 (1994) 5109–5113
DE-A 40 37 196
Doetschman et al, Nature 330 (1987) 576–578
Doetschman et al, Proc. Natl. Acad. Sci. USA 85 (1988) 8583–8587
Earhart et al, FEMS Microbiology Letters 6 (1979) 277–280
Ennen, J., et al, Proc. Natl. Acad. Sci. USA 91 (1994) 7207–7211
EP-A 0 173 251
EP-A 0 063 879
EP-A 0 128 018
EP-A 0 200 362
EP 0 219 874
EP 0 241 022
EP 0 364 926
Feigner et al, Proc. Natl. Acad. Sci. USA 84 (1987) 7413
Friedmann, T., Science 244 (1989) 1275
Goeddel, David V. (ed.), Methods of Enzymology 185, Gene Expression Technology, Academic Press 1991, section V
Grodberg and Dunn, J. Bacteriol. 170 (1988) 1245–1253
Hames, B. D., and Higgins, S. G., Nucleic acid hybridisation—a practical approach (1985) IRL Press, Oxford, England
Harlow and Lane eds., Antibodies: A laboratory manual (1988), Cold Spring Harbor Laboratories Press
Hsueh, Walker, et al, Cellular Immunology 159 (1994) 271–279
Huang and Terstappen, Nature 360 (1992) 745
Joag et al, Virology 200 (1994) 436–446
Kannagi et al, The Journal of Immunology, Vol. 140 (1988), No. 7, 2237–2242
Karber, G. 1931. Assay for statistical analysis of pharmacological experiments. Arch. Exper. Path. V. Pharmakol. 162, 148
Kikukawa, R., et al, J. Virol. 57 (1986) 1159–1162
Knuchel, Bednarik, et al, Journal of Acquired Immune Deficiency Syndromes, No. 7 (1994) 438–446
Köhler and Milstein, Nature 256 (1975) 495–497
Kraus, G., et al, Proc. Natl. Acad. Sci. USA 86 (1989) 2892–2896
Kucherlapati, Proc. in Nucl. Acids Res. and Mol. Biol. 36 (1989) 301
Levy, J. A., et al, Science 232 (1986) 998–1001
Luciw, P. A, et al, Nature 312 (1984) 760–763
Mackewicz et al, AIDS Research and Human Retroviruses, Vol. 8 (1992), No. 6, 1039–1050

Mackewicz et al, Lancet, 344 (1994) 1671–1673
Margolskee et al, Mol. Cell. Biol. 8 (1988) 2937
McLughlin, J. Virol. 62 (1988), 1963
Morgan 1993, RAC DATA MANAGEMENT REPORT, June 1993
Moss et al, Ann. Rev. Immunol. 5 (1987) 305
Mulligan, R. C. (1991) in Nobel Symposium 8: Ethiology of human disease at the DNA level (Lindsten, J. and Pattersun Editors) 143–189, Raven Press
Norley, S. G., et al, Biologicals 21 (1993) 251–258
Popovic, M., et al, Science 224 (1984) 497–500
Rand, Cruikshank, et al, J. Exp. Med. 173 (1991) 1521–1528
Rasmussen et al, Methods Enzymol. 139 (1987) 642
Sambrook et al, "Expression of cloned genes in *E. coli*" in Molecular Cloning: A laboratory manual (1989) Cold Spring Harbor Laboratory Press, New York, USA
Sanchez-Pescador, R., et al, Science 227 (1985) 484–492
Southern, E. M., J. Mol. Biol. 98 (1975) 503–517
Terstappen et al, Blood 77 (1991) 1218
Thomas and Capecchi, Cell 51 (1987) 503–512
Thomas et al, Cell 44 (1986) 419–428
Umesono et al, Cell 65 (1991) 1255–1266
U.S. Pat. No. 2,915,082
U.S. Pat. No. 5,399,346
U.S. Pat. No. 5,399,346
Wahl, G. M., et al, Proc. Natl. Acad. Sci. USA 76 (1979) 3683–3687
Walker, C. M., and Leighly, J. A., Immunology, Vol. 66 (1989) 628–630
Walker, Erickson, et al, Journal of Virology, Vol. 65 (1991) No. 11, 5921–5927
Walker, Moody, et al, Science, Vol. 234 (1986) 1563–1566
Walker, Thomson-Honnebier, et al, Cellular Immunology 137 (1991) 420–428
WO 89/06698
WO 93/0883
WO 94/23058
WO 94/28134

What is claimed is:

1. A method for identifying a compound capable of activating Immunodeficiency-virus Suppressing Lymphokine (ISL) production in human blood lymphocytes, said method comprising:
   a) isolating PBMC from healthy donors by Ficoll-gradient separation, isolating CD8+ cells from the PBMC by magnetic cell sorting to obtain a purified CD8+ cell preparation, testing the purity of the preparation by FACS analysis, and selecting the preparation having a content of approximately 95% CD8+ cells and 5% non-CD8+ contaminants to ensure adequate stimulation of the CD8+ cells;
   b) culturing
      1) the CD8+ cell preparation in a cell culture medium containing a substance to be tested for induction of expression of ISL activity at a concentration of 180 U/ml of cell culture medium, removing the cell culture medium after three days, and
      2) thereafter culturing the CD8+ cell preparation in a cell culture medium containing IL-2 at a concentration of 180 U/ml of cell culture medium for three days followed by centrifugation of the cell culture medium at 1,000 rpm to obtain a supernatant and to remove the CD8+ cell preparation, and sterile filtering and aliquoting the supernatant;
   c) detecting ISL expression induced by said compound in a sample comprising the supernatant or the CD8+ cell preparation;
   d) further identifying ISL-activating activity of said compound in an HIV-inhibition assay, said assay comprising
      1) incubating the supernatant of step b2) with CD8+-depleted PBMC in culture;
      2) infecting the CD8+-depleted PBMC in culture with HIV-1;
      3) thereafter culturing the CD8+-depleted PBMC; and
      4) quantitating inhibition of HIV-1 replication; and
   e) using a combination of said ISL expression of step c) and said inhibition of HIV-1 replication of step d) to indicate that said compound is capable of activating ISL production in human blood lymphocytes.

2. The method according to claim 1, wherein the detecting step (step c)) comprises
   a) an anti-ISL-antibody-based test comprising recognizing ISL;
   b) an in situ hybridization assay comprising recognizing nucleic acids encoding ISL;
   c) a colony or plaque hybridization assay comprising recognizing nucleic acids encoding ISL;
   d) a Northern hybridization assay comprising recognizing nucleic acids encoding ISL; or
   e) a PCR amplification assay comprising recognizing nucleic acids encoding ISL.

3. The method according to claim 1, wherein quantitating inhibition of HIV-1 replication (step d4)) comprises:
   a) culturing an HIV-1 susceptible indicator cell line with the supernatants of step d);
   b) determining viral replication by reverse transcriptase activity in a supernatant obtained from step d); and
   c) calculating inhibition of HIV-1 replication in the CD8+-depleted PBMC by comparing HIV-1 content of supernatants in an assay according to step b1) and b2), and HIV-1 content of supernatants in an assay according to step b1) and b2) where said compound is replaced with buffer.

* * * * *

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
      (A) LENGTH: 393 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION:1..393

(xi) SEQUENCE DESCRIPTION: SEQ ID NO: 1:

```
ATG CCC GAC CTC AAC TCC ACC ACT GAC TCT GCA GCC TCA GCC TCT GCA        48
Met Pro Asp Leu Asn Ser Thr Thr Asp Ser Ala Ala Ser Ala Ser Ala
 1               5                  10                  15

GCC AGT GAT GTT TCT GTA GAA TCC TCA GCA GAG GCC ACA GTC TAC ACG        96
Ala Ser Asp Val Ser Val Glu Ser Ser Ala Glu Ala Thr Val Tyr Thr
             20                  25                  30

GTG ACA CTG GAG AAG ATG TCT GCA GGG CTG GGC TTC AGC CTG GAA GGA       144
Val Thr Leu Glu Lys Met Ser Ala Gly Leu Gly Phe Ser Leu Glu Gly
         35                  40                  45

GGG AAG GGC TCC CTG CAT GGA GAC AAG CCT CTC ACC ATT AAC AGG ATT       192
Gly Lys Gly Ser Leu His Gly Asp Lys Pro Leu Thr Ile Asn Arg Ile
     50                  55                  60

TTC AAA GGA GCA GCC TCA GAA CAA AGT GAG ACA ATC CAG CCT GGA GAT       240
Phe Lys Gly Ala Ala Ser Glu Gln Ser Glu Thr Ile Gln Pro Gly Asp
 65                  70                  75                  80

GAA ATC TTG CAG CTG GCT GGC ACT GCC ATG CAG GGC CTC ACA CGG TTT       288
Glu Ile Leu Gln Leu Ala Gly Thr Ala Met Gln Gly Leu Thr Arg Phe
                 85                  90                  95

GAA GCC TGG AAC ATC ATC AAG GCC CTG CCT GAT GGA CCT GTC ACG ATT       336
Glu Ala Trp Asn Ile Ile Lys Ala Leu Pro Asp Gly Pro Val Thr Ile
            100                 105                 110

GTA ATT AGG AGG AAA AGC CTC CAA CCC AAG GAA ACC ACA GCT GCT GCA       384
Val Ile Arg Arg Lys Ser Leu Gln Pro Lys Glu Thr Thr Ala Ala Ala
```

```
                115                 120                 125
GAC TCC TAG                                                                393
Asp Ser  *
    130
```

(2) INFORMATION FOR SEQ ID NO: 2:

(i) SEQUENCE CHARACTERISTICS:
        (A) LENGTH: 130 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Pro Asp Leu Asn Ser Thr Thr Asp Ser Ala Ala Ser Ala Ser Ala
 1               5                  10                  15

Ala Ser Asp Val Ser Val Glu Ser Ser Ala Glu Ala Thr Val Tyr Thr
            20                  25                  30

Val Thr Leu Glu Lys Met Ser Ala Gly Leu Gly Phe Ser Leu Glu Gly
        35                  40                  45

Gly Lys Gly Ser Leu His Gly Asp Lys Pro Leu Thr Ile Asn Arg Ile
    50                  55                  60

Phe Lys Gly Ala Ala Ser Glu Gln Ser Glu Thr Ile Gln Pro Gly Asp
65                  70                  75                  80

Glu Ile Leu Gln Leu Ala Gly Thr Ala Met Gln Gly Leu Thr Arg Phe
                85                  90                  95

Glu Ala Trp Asn Ile Ile Lys Ala Leu Pro Asp Gly Pro Val Thr Ile
            100                 105                 110

Val Ile Arg Arg Lys Ser Leu Gln Pro Lys Glu Thr Thr Ala Ala Ala
        115                 120                 125

Asp Ser
    130
```

(2) INFORMATION FOR SEQ ID NO: 3:

(i) SEQUENCE CHARACTERISTICS:
        (A) LENGTH: 2151 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION:783..1175

(ix) FEATURE:
        (A) NAME/KEY: mat_peptide
        (B) LOCATION:783

(xi) SEQUENCE DESCRIPTION: SEQ ID NO: 3:

```
TTCCTCGAGA GCTGTCAACA CAGGCTGAGG AATCTCAAGG CCCAGTGCTC AAGATGCCTA      60

GCCAGCGAGC ACGGAGCTTC CCCCTGACCA GGTCCCAGTC CTGTGAGACG AAGCTACTTG     120

ACGAAAAGAC CAGCAAACTC TATTCTATCA CCAGCCAGTG TCATCGGCTG TCATGAAATC     180

CTTGCTGTGC CTTCCATCTT CTATCTCCTG TGCCCAGACT CCCTGCATCC CCAAGGAAGG     240

GGCATCTCCA ACATCATCAT CCAACGAAGA CTCAGCTGCA AATGGTTCTG CTGAAACATC     300

TGCCTTGGAC ACGGGGTTCT CGCTCAACCT TTCAGAGCTG AGAGAATATA CAGAGGGTCT     360

CACGGAAGCC AAGGAAGACG ATGATGGGGA CCACAGTTCC TTCAGTCTGG TCAGTCCGTT     420
```

```
ATCTCCCTGC TGAGCTCAGA AGAATTAAAA AAACTCATCG AGGAGGTGAA GGTTCTGGAT        480

GAAGCAACAT TAAAGCAATT AGACGGCATC CATGTCACCA TCTTACACAA GGAGGAAGGT        540

GCTGGTCTTG GGTTCAGCTT GGCAGGAGGA GCAGATCTAG AAAACAAGGT GATTACGGTT        600

CACAGAGTGT TTCCAAATGG GCTGGCCTCC CAGGAAGGGA CTATTCAGAA GGGCAATGAG        660

GTTCTTTCCA TCAACGGCAA GTCTCTCAAG GGACCACGC ACCATGATGC CTTGGCCATC         720

CTCCGCCAAG CTCGAGAGCC CAGGCAAGCT GTGATTGTCA AAGGAAGCT GACTCCAGAG         780

CC ATG CCC GAC CTC AAC TCC TCC ACT GAC TCT GCA GCC TCA GCC TCT           827
   Met Pro Asp Leu Asn Ser Ser Thr Asp Ser Ala Ala Ser Ala Ser
     1               5                  10                 15

GCA GCC AGT GAT GTT TCT GTA GAA TCT ACA GCA GAG GCC ACA GTC TGC          875
Ala Ala Ser Asp Val Ser Val Glu Ser Thr Ala Glu Ala Thr Val Cys
                20                  25                  30

ACG GTG ACA CTG GAG AAG ATG TCG GCA GGG CTG GGC TTC AGC CTG GAA          923
Thr Val Thr Leu Glu Lys Met Ser Ala Gly Leu Gly Phe Ser Leu Glu
                35                  40                  45

GGA GGG AAG GGC TCC CTA CAC GGA GAC AAG CCT CTC ACC ATT AAC AGG          971
Gly Gly Lys Gly Ser Leu His Gly Asp Lys Pro Leu Thr Ile Asn Arg
            50                  55                  60

ATT TTC AAA GGA GCA GCC TCA GAA CAA AGT GAG ACA GTC CAG CCT GGA         1019
Ile Phe Lys Gly Ala Ala Ser Glu Gln Ser Glu Thr Val Gln Pro Gly
 65                  70                  75

GAT GAA ATC TTG CAG CTG GGT GGC ACT GCC ATG CAG GGC CTC ACA CGG         1067
Asp Glu Ile Leu Gln Leu Gly Gly Thr Ala Met Gln Gly Leu Thr Arg
 80                  85                  90                  95

TTT GAA GCC TGG AAC ATC ATC AAG GCA CTG CCT GAT GGA CCT GTC ACG         1115
Phe Glu Ala Trp Asn Ile Ile Lys Ala Leu Pro Asp Gly Pro Val Thr
                100                 105                 110

ATT GTC ATC AGG AGA AAA AGC CTC CAG TCC AAG GAA ACC ACA GCT GCT         1163
Ile Val Ile Arg Arg Lys Ser Leu Gln Ser Lys Glu Thr Thr Ala Ala
                115                 120                 125

GGA GAC TCC TAG GCAGGACATG CTGAAGCCAA AGCCAATAAC ACACAGCTAA             1215
Gly Asp Ser  *
            130

CACACAGCTC CCATAACCGC TGATTCTCAG GGTCTCTGCT GCCGCCCCAC CCAGATGGGG       1275

GAAAGCACAG GTGGGCTTCC CAGTGGCTGC TGCCCAGGCC CAGACCTTCT AGGACGCCAC       1335

CCAGCAAAAG GTTGTTCCTA AATAAGGGC AGAGTCACAC TGGGGCAGCT GATACAAATT        1395

GCAGACTGTG TAAAAGAGA GCTTAATGAT AATATTGTGG TGCCACAAAT AAAATGGATT        1455

TATTAGAATT TCATATGACA TTCATGCCTG GCTTCGCAAA ATGTTTCAAG TACTGTAACT       1515

GTGTCATGAT TCACCCCCAA ACAGTGACAT TTATTTTTCT CATGAATCTG CAATGTGGGC       1575

AGAGATTGGA ATGGGCAGCT CATCTCTGTC CCACTTGGCA TCAGCTGGCG TCATGCAAAG       1635

TCATGCAAAG GCTGGGACCA CGTGAGATCA TTCACTCATA CATCTGGCCG TTGATGTTGG      1695

CTGGGAACTC ACCTGGGGCT GCTGGCCTGA ATGCTTATAG GTGCCTCTC CTTGTGGCCT       1755

GGGCTCCTCA CAACATGGTG TCTGGATTCC CAGGATGAGC ATCCCAGGAT CGCAAGAGCC      1815

ACGTAGAAGC TGCATCTTGT TTATACCTTT GCCTTGGAAG TTGCATGGCA TCACCTCCAC      1875

CATACTCCAT CAGTTAGAGC TGACACAAAC CTGCCTGGGT TTAAGGGGAG AGGAAATATT      1935

GCTGGGGTCA TTTATGAAAA ATACAGTTTG TCACATGAAA CATTTGCAAA ATTGTTTTTG     1995

GTTGGATTGG AGAAGTAATC CTAGGGAAGG GTGGTGGAGC CAGTAAATAG AGGAGTACAG     2055

GTGAAGCACC AAGCTCAAAG CGTGGACAGG TGTGCCGACA GAAGGAACCA GCGTGTATAT     2115
```

GAGGGTATCA AATAAAATTG CTACTACTTA CCTACC                                    2151

(2) INFORMATION FOR SEQ ID NO: 4:

(i) SEQUENCE CHARACTERISTICS:
        (A) LENGTH: 130 amino acids
        (B) TYPE: amino acid
        (D) TOPOLOGY: linear (ii) MOLECULE TYPE: protein (xi) SEQUENCE DESCRIPTION: SEQ ID NO: 4:

Met Pro Asp Leu Asn Ser Ser Thr Asp Ser Ala Ala Ser Ala Ser Ala
 1               5                  10                  15

Ala Ser Asp Val Ser Val Glu Ser Thr Ala Glu Ala Thr Val Cys Thr
             20                  25                  30

Val Thr Leu Glu Lys Met Ser Ala Gly Leu Gly Phe Ser Leu Glu Gly
         35                  40                  45

Gly Lys Gly Ser Leu His Gly Asp Lys Pro Leu Thr Ile Asn Arg Ile
     50                  55                  60

Phe Lys Gly Ala Ala Ser Glu Gln Ser Glu Thr Val Gln Pro Gly Asp
 65                  70                  75                  80

Glu Ile Leu Gln Leu Gly Gly Thr Ala Met Gln Gly Leu Thr Arg Phe
                 85                  90                  95

Glu Ala Trp Asn Ile Ile Lys Ala Leu Pro Asp Gly Pro Val Thr Ile
            100                 105                 110

Val Ile Arg Arg Lys Ser Leu Gln Ser Lys Glu Thr Thr Ala Ala Gly
        115                 120                 125

Asp Ser
    130

(2) INFORMATION FOR SEQ ID NO: 5:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

GCTGCCTCTC ATATGGACCT CAACTCCTCC ACTGACTCT                                   39

(2) INFORMATION FOR SEQ ID NO: 6:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

GATGGACAGG GATCCCTAGG AGTCTCCAGC AGCTGTGG                                    38

(2) INFORMATION FOR SEQ ID NO: 7:

(i) SEQUENCE CHARACTERISTICS:
        (A) LENGTH: 9737 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 7:

```
CTGGAAGGGC TAATTTGGTC CCAAAGAAGA CAAGAGATCC TTGATCTGTG GATCTACCAC      60
ACACAAGGCT ACTTCCCTGA TTGGCAGAAT TACACACCAG GGCCAGGGAT CAGATATCCA     120
CTGACCTTTG GATGGTGCTT CAAGCTAGTA CCAGTTGAGC CAGAGAAGGT AGAAGAGGCC     180
AATGAAGGAG AGAACAACAG CTTGTTACAC CCTATGAGCC TGCATGGGAT GGAGGACGCG     240
GAGAAAGAAG TGTTAGTGTG GAGGTTTGAC AGCAAACTAG CATTTCATCA CATGGCCCGA     300
GAGCTGCATC CGGAGTACTA CAAAGACTGC TGACATCGAG CTTTCTACAA GGGACTTTCC     360
GCTGGGGACT TTCCAGGGAG GCGTGGCCTG GCGGGACTG GGGAGTGGCG TCCCTCAGAT     420
GCTGCATATA AGCAGCTGCT TTTTGCCTGT ACTGGGTCTC TCTGGTTAGA CCAGATCTGA     480
GCCTGGGAGC TCTCTGGCTA ACTAGGGAAC CCACTGCTTA AGCCTCAATA AAGCTTGCCT     540
TGAGTGCTTC AAGTAGTGTG TGCCCGTCTG TTGTGTGACT CTGGTAACTA GAGATCCCTC     600
AGACCCTTTT AGTCAGTGTG GAAAAATCTC TAGCAGTGGC GCCCGAACAG GGACGCGAAA     660
GCGAAAGTAG AACCAGAGGA GCTCTCTCGA CGCAGGACTC GGCTTGCTGA AGCGCGCACA     720
GCAAGAGGCG AGGGGCGGCG ACTGGTGAGT ACGCCAATTT TGACTAGCG GAGGCTAGAA     780
GGAGAGAGAG ATGGGTGCGA GAGCGTCGGT ATTAAGCGGG GGAGAATTAG ATAAATGGGA     840
AAAAATTCGG TTAAGGCCAG GGGGAAAGAA AAAATATAAG TTAAAACATA TAGTATGGGC     900
AAGCAGGGAG CTAGAACGAT TCGCAGTCAA TCCTGGCCTG TTAGAAACAT CAGAAGGCTG     960
CAGACAAATA TTGGGACAGC TACAGCCATC CCTTCAGACA GGATCAGAAG AACTTAGATC    1020
ATTATATAAT ACAGTAGCAA CCCTCTATTG TGTACATCAA AGGATAGATG TAAAAGACAC    1080
CAAGGAAGCT TTAGAGAAGA TAGGAGAAGA GCAAAACAAA AGTAAGAAAA AGGCACAGCA    1140
AGCAGCAGCT GCAGCTGGCA CAGGAAACAG CAGCCAGGTC AGCCAAAATT ACCCTATAGT    1200
GCAGAACCTA CAGGGGCAAA TGGTACATCA GGCCATATCA CCTAGAACTT TAAATGCATG    1260
GGTAAAAGTA GTAGAAGAAA AGGCTTTCAG CCCAGAAGTA ATACCCATGT TTTCAGCATT    1320
ATCAGAAGGA GCCACCCCAC AAGATTTAAA CACCATGCTA AACACAGTGG GGGGACATCA    1380
AGCAGCCATG CAAATGTTAA AAGAGACTAT CAATGAGGAA GCTGCAGAAT GGGATAGAGT    1440
GCATCCAGTG CATGCAGGGC CTATTGCACC AGGCCAAATG AGAGAACCAA GGGGAAGTGA    1500
CATAGCAGGA ACTACTAGTA CCCTTCAGGA ACAAATAGGA TGGATGACAA ATAATCCACC    1560
TATCCCAGTA GGAGAAATCT ATAAAAGATG GATAATCCTG GGATTAAATA AAATAGTAAG    1620
AATGTATAGC CCTACCAGCA TTCTGGACAT AAGACAAGGA CCAAAGGAAC CCTTTAGAGA    1680
TTATGTAGAC CGGTTCTATA AAACTCTAAG AGCCGAACAA GCTTCACAGG ATGTAAAAAA    1740
TTGGATGACA GAAACCTTGT TGGTCCAAAA TGCAAACCCA GATTGTAAGA CTATTTTAAA    1800
AGCATTGGGA CCAGCAGCTA CACTAGAAGA AATGATGACA GCATGTCAGG GAGTGGGGGG    1860
ACCCGGCCAT AAAGCAAGAG TTTTGGCTGA AGCCATGAGC CAAGTAACAA ATCCAGCTAA    1920
CATAATGATG CAGAGAGGCA ATTTTAGGAA CCAAAGAAAG ACTGTTAAGT GTTTCAATTG    1980
TGGCAAAGAA GGGCACATAG CCAAAAATTG CAGGGCCCCT AGGAAAAAGG CTGTTGGAG    2040
ATGTGGAAGG GAAGGACACC AAATGAAAGA TTGCACTGAG AGACAGGCTA ATTTTTTAGG    2100
GAAGATCTGG CCTTCCTACA AGGGAAGGCC AGGGAATTTT CTTCAGAGCA GACCAGAGCC    2160
AACAGCCCCA CCAGAAGAGA GCTTCAGGTT TGGGGAGGAG AAAACAACTC CCTCTCAGAA    2220
```

```
GCAGGAGCCG ATAGACAAGG AACTGTATCC TTTAACTTCC CTCAGATCAC TCTTTGGCAA    2280

CGACCCCTCG TCACAATAAG GATAGGGGGG CAACTAAAGG AAGCTCTATT AGATACAGGA    2340

GCAGATGATA CAGTATTAGA AGAAATGAAT TTGCCAGGAA AATGGAAACC AAAAATGATA    2400

GGGGGAATTG GAGGTTTTAT CAAAGTAAGA CAGTACGATC AGATACCTGT AGAAATCTGT    2460

GGACATAAAG CTATAGGTAC AGTATTAGTA GGACCTACAC CTGTCAACAT AATTGGAAGA    2520

AATCTGTTGA CTCAGATTGG TTGTACTTTA AATTTCCCCA TTAGTCCTAT TGAAACTGTA    2580

CCAGTAAAAT TAAAGCCAGG AATGGATGGC CCAAAAGTTA AGCAATGGCC ATTGACAGAA    2640

GAAAAAATAA AAGCATTAGT AGAGATATGT ACAGAAATGG AAAAGGAAGG GAAAATTTCA    2700

AAAATTGGGC CTGAAAATCC ATACAATACT CCAGTATTTG CTATAAAGAA AAAAGACAGT    2760

ACTAAATGGA GAAAACTAGT AGATTTCAGA GAACTTAATA AAAGAACTCA AGACTTCTGG    2820

GAAGTTCAGT TAGGAATACC ACACCCCGCA GGGTTAAAAA AGAAAAAATC AGTAACAGTA    2880

TTGGATGTGG GTGATGCATA CTTTTCAGTT CCCTTAGATA AAGACTTTAG AAAGTATACT    2940

GCATTTACCA TACCTAGTAT AAACAATGAG ACACCAGGGA TTAGATATCA GTACAATGTG    3000

CTGCCACAGG GATGGAAAGG ATCACCAGCA ATATTCCAAA GTAGCATGAC AAAAATCTTA    3060

GAGCCTTTTA GAAAACAGAA TCCAGACATA GTTATCTATC AATACATGGA TGATTTGTAT    3120

GTAGGATCTG ACTTAGAAAT AGGGCAGCAT AGAACAAAAA TAGAGGAACT GAGACAGCAT    3180

CTGTTGAGGT GGGGATTTAC CACACCAGAC AAAAAACATC AGAAAGAACC TCCATTCCTT    3240

TGGATGGGTT ATGAACTCCA TCCTGATAAA TGGACAGTAC AGCCTATAAT GCTGCCAGAA    3300

AAAGACAGCT GGACTGTCAA TGACATACAG AAGTTAGTGG GAAAATTGAA TTGGGCAAGT    3360

CAGATTTATG CAGGGATTAA AGTAAAGCAG TTATGTAAAC TCCTTAGAGG AACCAAAGCA    3420

CTAACAGAAG TAATACCACT AACAGAAGAA GCAGAGCTAG AACTGGCAGA AAACAGGGAG    3480

ATTCTAAAAG AACCAGTACA TGAAGTATAT TATGACCCAT CAAAAGACTT AGTAGCAGAA    3540

ATACAGAAGC AGGGGCAAGG CCAATGGACA TATCAAATTT ATCAAGAGCC ATTTAAAAAT    3600

CTGAAAACAG GAAAGTATGC AAGGATGAGG GGTGCCCACA CTAATGATGT AAAACAGTTA    3660

ACAGAGGCAG TGCAAAAAGT ATCCACAGAA AGCATAGTAA TATGGGGAAA GATTCCTAAA    3720

TTTAAACTAC CCATACAAAA GGAAACATGG GAAGCATGGT GGATGGAGTA TTGGCAAGCT    3780

ACCTGGATTC CTGAGTGGGA GTTTGTCAAT ACCCCTCCCT TAGTGAAATT ATGGTACCAG    3840

TTAGAGAAAG AACCCATAGT AGGAGCAGAA ACTTTCTATG TAGATGGGGC AGCTAATAGG    3900

GAGACTAAAT TAGGAAAAGC AGGATATGTT ACTGACAGAG GAAGACAAAA AGTTGTCTCC    3960

ATAGCTGACA CAACAAATCA GAAGACTGAA TTACAAGCAA TTCATCTAGC TTTGCAGGAT    4020

TCGGGATTAG AAGTAAACAT AGTAACAGAC TCACAATATG CATTAGGAAT CATTCAAGCA    4080

CAACCAGATA AGAGTGAATC AGAGTTAGTC AGTCAAATAA TAGAGCAGTT AATAAAAAAG    4140

GAAAAGGTCT ACCTGGCATG GGTACCAGCA CACAAAGGAA TTGGAGGAAA TGAACAAGTA    4200

GATAAATTAG TCAGTGCTGG AATCAGGAAA GTACTATTTT TGAATGGAAT AGATAAGGCC    4260

CAAGAAGAAC ATGAGAAATA TCACAGTAAT TGGAGAGCAA TGGCTAGTGA TTTTAACCTG    4320

CCACCTGTAG TAGCAAAAGA AATAGTAGCC AGCTGTGATA AATGTCAGCT AAAAGGAGAA    4380

GCCATGCATG GACAAGTAGA CTGTAGTCCA GGAATATGGC AACTAGATTG TACACATCTA    4440

GAAGGAAAAA TTATCCTGGT AGCAGTTCAT GTAGCCAGTG GATATATAGA AGCAGAAGTT    4500

ATTCCAGCAG AGACAGGGCA GGAAACAGCA TATTTTCTCT TAAAATTAGC AGGAAGATGG    4560

CCAGTAAAAA CAATACATAC AGACAATGGC AGCAATTTCA CCAGTACTAC GGTTAAGGCC    4620
```

```
GCCTGTTGGT GGGCAGGGAT CAAGCAGGAA TTTGGCATTC CCTACAATCC CCAAAGTCAA   4680

GGAGTAGTAG AATCTATGAA TAATGAATTA AAGAAAATTA TAGGACAGGT AAGAGATCAG   4740

GCTGAACACC TTAAGACAGC AGTACAAATG GCAGTATTCA TCCACAATTT TAAAAGAAAA   4800

GGGGGGATTG GGGGATACAG TGCAGGGGAA AGAATAGTAG ACATAATAGC AACAGACATA   4860

CAAACTAAAG AACTACAAAA GCAAATTACA AAAATTCAAA ATTTTCGGGT TTATTACAGG   4920

GACAACAAAG ATCCCCTTTG GAAAGGACCA GCAAAGCTTC TCTGGAAAGG TGAAGGGGCA   4980

GTAGTAATAC AAGATAATAG TGACATAAAA GTAGTGCCAA GAAGAAAAGC AAAAATCATT   5040

AGGGATTATG GAAAACAGAT GGCAGGTGAT GATTGTGTGG CAAGTAGACA GGATGAGGAT   5100

TAGAACATGG AAAAGTTTAG TAAAACACCA TATGTATATT TCAAAGAAAG CTAAAGGATG   5160

GTTTTATAGA CATCACTATG AAAGTACTCA TCCAAGAGTA AGTTCAGAAG TACACATCCC   5220

CCTAGGGGAT GCTAAATTGG TAATAACAAC ATATTGGGGT CTGCATACAG GAGAAAGAGA   5280

ATGGCATTTG GGCCAGGGAG TCGCCATAGA ATGGAGGAAA AAGAAATATA GCACACAAGT   5340

AGACCCTGGC CTAGCAGACC AACTAATTCA TCTGCATTAT TTTGATTGTT TTTCAGAATC   5400

TGCTATAAAA AATGCCATAT TAGGATATAG AGTTAGTCCT AGGTGTGAAT ATCAAGCAGG   5460

ACATAACAAG GTAGGATCTC TACAATACTT GGCACTAGCA GCATTAATAA CACCAAAAAA   5520

GACAAAGCCA CCTTTGCCTA GTGTTAAGAA ACTGACAGAG GATAGATGGA ACAAGCCCCA   5580

GAAGACCAAG GGCCACAGAG GGAGCCATAC AATGAATGGA CACTAGAGCT TTTAGAGGAG   5640

CTTAAGAGAG AAGCTGTTAG ACATTTTCCT AGGCCATGGC TCCATAGCTT AGGACAATAT   5700

ATCTATGAAA CTTATGGGGA TACTTGGGCA GGAGTGGAAG CCATAATAAG AATTCTGCAA   5760

CAACTGCTGT TTATTCATTT CAGAATTGGG TGTCAACATA GCAGAATAGG CATTATTCAA   5820

CAGAGGAGAG CAAGAAGAAA TGGAGCCAGT AGATCCTAAT CTAGAGCCCT GGAAGCATCC   5880

AGGAAGTCAG CCTAGGACTG CTTGTAACAA TTGCTATTGT AAAAAGTGTT GCTTTCATTG   5940

CTACGCGTGT TTCACAAGAA AAGGCTTAGG CATCTCCTAT GGCAGGAAGA AGCGGAGACA   6000

GCGACGAAGA GCTCCTCAGG ACAGTCAGAC TCATCAAGCT TCTCTATCAA AGCAGTAAGT   6060

AGTAAATGTA ATGCAATCTT TACAAATATT AGCAATAGTA TCATTAGTAG TAGTAGCAAT   6120

AATAGCAATA GTTGTGTGGA CCATAGTACT CATAGAATAT AGGAAAATAT TAAGACAAAG   6180

AAAATAGACA GATTAATTGA TAGAATAAGA GAAAAGCAG AAGACAGTGG CAATGAAAGT   6240

GAAGGGGACC AGGAGGAATT ATCAGCACTT GTGGAGATGG GGCACCTTGC TCCTTGGGAT   6300

GTTGATGATC TGTAGTGCTA CAGAAAAATT GTGGGTCACA GTTTATTATG GAGTACCTGT   6360

GTGGAAAGAA GCAACTACCA CTCTATTTTG TGCATCAGAT GCTAGAGCAT ATGATACAGA   6420

GGTACATAAT GTTTGGGCCA CACATGCCTG TGTACCCACA GACCCCAACC CACAAGAAGT   6480

AGTATTGGGA AATGTGACAG AAAATTTTAA CATGTGGAAA AATAACATGG TAGAACAGAT   6540

GCAGGAGGAT ATAATCAGTT TATGGGATCA AAGCCTAAAG CCATGTGTAA AATTAACCCC   6600

ACTCTGTGTT ACTTTAAATT GCACTGATTT GGGGAAGGCT ACTAATACCA ATAGTAGTAA   6660

TTGGAAAGAA GAAATAAAAG GAGAAATAAA AAACTGCTCT TTCAATATCA CCACAAGCAT   6720

AAGAGATAAG ATTCAGAAAG AAAATGCACT TTTTCGTAAC CTTGATGTAG TACCAATAGA   6780

TAATGCTAGT ACTACTACCA ACTATACCAA CTATAGGTTG ATACATTGTA ACAGATCAGT   6840

CATTACACAG GCCTGTCCAA AGGTATCATT TGAGCCAATT CCCATACATT ATTGTACCCC   6900

GGCTGGTTTT GCGATTCTAA AGTGTAATAA TAAAACGTTC AATGGAAAAG GACCATGTAC   6960
```

```
AAATGTCAGC ACAGTACAAT GTACACATGG AATTAGGCCA ATAGTGTCAA CTCAACTGCT    7020

GTTAAATGGC AGTCTAGCAG AAGAAGAGGT AGTAATTAGA TCTGACAATT TCACGAACAA    7080

TGCTAAAACC ATAATAGTAC AGCTGAATGA ATCTGTAGCA ATTAACTGTA CAAGACCCAA    7140

CAACAATACA AGAAAAAGTA TCTATATAGG ACCAGGGAGA GCATTTCATA CAACAGGAAG    7200

AATAATAGGA GATATAAGAA AAGCACATTG TAACATTAGT AGAGCACAAT GGAATAACAC    7260

TTTAGAACAG ATAGTTAAAA AATTAAGAGA ACAGTTTGGG AATAATAAAA CAATAGTCTT    7320

TAATCAATCC TCAGGAGGGG ACCCAGAAAT TGTAATGCAC AGTTTTAATT GTAGAGGGGA    7380

ATTTTTCTAC TGTAATACAA CACAACTGTT AATAATACA TGGAGGTTAA ATCACACTGA    7440

AGGAACTAAA GGAAATGACA CAATCATACT CCCATGTAGA ATAAAACAAA TTATAAACAT    7500

GTGGCAGGAA GTAGGAAAAG CAATGTATGC CCCTCCCATT GGAGGACAAA TTAGTTGTTC    7560

ATCAAATATT ACAGGGCTGC TATTAACAAG AGATGGTGGT ACAAATGTAA CTAATGACAC    7620

CGAGGTCTTC AGACCTGGAG GAGGAGATAT GAGGGACAAT TGGAGAAGTG AATTATATAA    7680

ATATAAAGTA ATAAAAATTG AACCATTAGG AATAGCACCC ACCAAGGCAA AGAGAAGAGT    7740

GGTGCAGAGA GAAAAAAGAG CAGTGGGAAT AGTAGGAGCT ATGTTCCTTG GGTTCTTGGG    7800

AGCAGCAGGA AGCACTATGG GCGCAGTGTC ATTGACGCTG ACGGTACAGG CCAGACAATT    7860

ATTGTCTGGT ATAGTGCAAC AGCAGAACAA TTTGCTGAGG GCTATTGAGG CGCAACAACA    7920

TCTGTTGCAA CTCACAGTCT GGGGCATCAA GCAGCTCCAG GCAAGAGTCC TGGCTGTGGA    7980

AAGATACCTA AGGGATCAAC AGCTCCTAGG GATTTGGGGT TGCTCTGGAA AACTCATTTG    8040

CACCACTGCT GTGCCTTGGA ATGCTAGTTG GAGTAATAAA TCTCTGGAAG ACATTTGGGA    8100

TAACATGACC TGGATGCAGT GGGAAAGAGA AATTGACAAT TACACAAACA CAATATACAC    8160

CTTACTTGAA GAATCGCAGA ACCAACAAGA AAAGAATGAA CAAGAATTAT TAGAATTGGA    8220

TAAGTGGGCA AGTTTGTGGA ATTGGTTTAG CATAACAAAC TGGCTGTGGT ATATAAAGAT    8280

ATTCATAATG ATAGTAGGAG GCTTGGTAGG TTTAAGAATA GTTTTTGCTG TGCTTTCTAT    8340

AGTGAATAGA GTTAGGCAGG GATACTCACC ATTGTCATTT CAGACCCGCC TCCCAGTCCC    8400

GAGGGGACCC GACAGGCCCG ACGGAATCGA AGAAGAAGGT GGAGAGAGAG ACAGAGACAG    8460

ATCCGTTCGA TTAGTGGATG GATTCTTAGC ACTTATCTGG GAAGATCTGC GGAGCCTGTG    8520

CCTCTTCAGC TACCGCCGCT TGAGAGACTT ACTCTTGATT GCAGCGAGGA CTGTGGAAAT    8580

TCTGGGCAC AGGGGGTGGG AAGCCCTCAA ATATTGGTGG AGTCTCCTGC AGTATTGGAT    8640

TCAGGAACTA AGAATAGTG CTGTTAGCTG GCTCAACGCC ACAGCTATAG CAGTAACTGA    8700

GGGGACAGAT AGGGTTATAG AAGTAGCACA AAGAGCTTAT AGAGCTATTC TCCACATACA    8760

TAGAAGAATT AGACAGGGCT TGGAAAGGCT TTTGCTATAA GATGGGTGGC AAGTGGTCAA    8820

AACGTAGTAT GGGTGGATGG TCTGCTATAA GGGAAAGAAT GAGACGAGCT GAGCCACGAG    8880

CTGAGCCAGC AGCAGATGGG GTGGGAGCAG TATCTCGAGA CCTGGAAAAA CATGGAGCAA    8940

TCACAAGTAG CAATACAGCA GCTACTAATG CTGATTGTGC CTGGCTAGAA GCACAAGAGG    9000

AGGAAGAGGT GGGTTTTCCA GTCAGACCTC AGGTACCTTT AAGACCAATG ACTTACAAGG    9060

CAGCTTTAGA TATTAGCCAC TTTTTAAAAG AAAAGGGGGG ACTGGAAGGG CTAATTTGGT    9120

CCCAAAGAAG ACAAGAGATC CTTGATCTGT GGATCTACCA CACACAAGGC TACTTCCCTG    9180

ATTGGCAGAA TTACACACCA GGGCCAGGGA TCAGATATCC ACTGACCTTT GGATGGTGCT    9240

TCAAGCTAGT ACCAGTTGAG CCAGAGAAGG TAGAAGAGGC CAATGAAGGA GAACAACAA    9300

GCTTGTTACA CCCTATGAGC CTGCATGGGA TGGAGGACGC GGAGAAAGAA GTGTTAGTGT    9360
```

```
GGAGGTTTGA CAGCAAACTA GCATTTCATC ACATGGCCCG AGAGCTGCAT CCGGAGTACT      9420

ACAAAGACTG CTGACATCGA GCTTTCTACA AGGGACTTTC CGCTGGGGAC TTTCCAGGGA      9480

GGCGTGGCCT GGGCGGGACT GGGGAGTGGC GTCCCTCAGA TGCTGCATAT AAGCAGCTGC      9540

TTTTTGCCTG TACTGGGTCT CTCTGGTTAG ACCAGATCTG AGCCTGGGAG CTCTCTGGCT      9600

AACTAGGGAA CCCACTGCTT AAGCCTCAAT AAAGCTTGCC TTGAGTGCTT CAAGTAGTGT      9660

GTGCCCGTCT GTTGTGTGAC TCTGGTAACT AGAGATCCCT CAGACCCTTT TAGTCAGTGT      9720

GGAAAAATCT CTAGCAG                                                    9737

(2) INFORMATION FOR SEQ ID NO: 8:

(i) SEQUENCE CHARACTERISTICS:
        (A) LENGTH: 4527 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 8:

GAATTCTGCA ACAACTGCTG TTTATTCATT TCAGAATTGG GTGCCAACAT AGCAGAATAG        60

GCATTACTCG ACAGAGGAGA GCAAGAAATG GAGCCAGTAG ATCCTAACCT AGAGCCCTGG       120

AAGCATCCAG GAAGTCAGCC TAGGACTGCT TGCACCAACT GCTATTGTAA AAAGTGTTGC       180

TTTCATTGCC AAGTTTGCTT CATAACAAAA GGCTTAGGCA TATCCTATGG CAGGAAGAAG       240

CGGAGGCAGC GACAGAGAGC TCCTGACAGC AGTCAGAATC ATCAAGATTC TCTATCAAAG       300

CAGTAAGTAG TACATGTAAT GTAATCTTTA ACAATATTAG CAATAGTAGC AATAGTAGTA       360

GTAACAATAA TAGCAATAGT TATATGGACC ATAGTATTAA TAAAATATAG GAAAATATTA       420

AGACAAAGAA AAATAGACAG ATTAATTGAT AGAATAAGAG AAAGAGCAGA AGACAGTGGC       480

AATGAGAGCG AGGGAGACCA GGAAGAATTA TCAGTGCTTG TGGAGATGGG GCACGATGCT       540

CCTTGGGATG TTAATGATCT GTAGTGCTGC AGAAAATTTG TGGGTCACAG TTTATTATGG       600

GGTACCTGTG TGGAAAGATG CAACCACTAC TCTATTTTGT GCATCAGATG CTAAAGCATA       660

TGATACAGAG GTACATAATG TTTGGGCCAC ACATGCCTGT GTACCCACAG ACCCCAACCC       720

CCAAGAAGTA GTATTGGGAA ATGTGACAGA AAATTTTAAC ATGTGGAAAA ATAACATGGT       780

AGACCAGATG CATGAGGATA TAGTCAGTTT ATGGGATCAA AGCCTAAAGC CATGTGTAAA       840

ATTAACCCCA CTCTGTGTTA CTTTAAATTG CACTGATTAT TTGGGGAATG CTACTAATAC       900

CAACAATAGT AGTGGGGGAA CGGTGGAGAA AGAAGAAATA AAAAACTGCT CTTTCAATAT       960

CACCACAGGC ATAAGAGATA AGGTACAGAA GGCATATGCA TATTTTTATA AACTTGATGT      1020

AGTACCAATA GATGATGATA ATACTAATAC CAGCTATAGG TTGATACATT GTAATTCCTC      1080

AGTCATTACA CAGACCTGTC CAAAGGTATC CTTTGAGCCA ATTCCTATAC ATTATTGTGC      1140

CCCGGCTGGT TTTGCGATTC TAAAGTGTAA TAATAAGAAG TTCAGTGGAA AAGGTCAATG      1200

TACAAATGTC AGCACAGTAC AATGTACACA TGGAATTAAG CCAGTAGTGT CAACTCAACT      1260

GCTGTTAAAT GGCAGTCTAG CAGAAGAAGA GGTAGTAATT AGATCTGACA ATTTCACGAA      1320

CAATGCTAAA ACCATATTAG TACAGCTGAA TGTATCTGTA GAATTAATT GTACAAGACC       1380

CAACAACAAT AGAAGAAGAA GGATAACTAG TGGACCAGGG AAAGTACTTT ATACAACAGG      1440

AGAAATAATA GGAGATATAA GAAAAGCATA TTGTAACATT AGTAGAGCAA AATGGAATAA      1500

AACTTTAGAA CAGGTAGCTA CAAAATTAAG AGAACAATTT GGGAATAAAA CAATAGTATT      1560
```

-continued

```
TAAACAATCC TCAGGAGGAG ACCCAGAAAT TGTAATGCAC AGTTTTAATT GTAGAGGGGA   1620

ATTTTTCTAC TGTAATACAA CAAAACTGTT AATAGTACT TGGAATGAAA ATAGTACTTG    1680

GAATGCTACT GGAAATGACA CTATCACACT CCCATGTAGA ATAAAACAAA TTATAAACAT   1740

GTGGCAGGAA GTAGGAAAAG CAATGTATGC CCCTCCCATC GAAGGACAAA TTAGATGTTC   1800

ATCAAATATT ACAGGGCTGC TATTAACAAG AGATGGTGGT GGTGACAAGA ACAGTACCAC   1860

CGAGATCTTT AGACCTGCAG GAGGAAATAT GAAGGACAAT TGGAGAAGTG AATTATATAA   1920

ATATAAAGTA GTAAAAATTG AACCATTAGG AGTAGCACCC ACCAAGGCAA AGAGAAGAGT   1980

GGTGCAAAGA GAAAAAGAG CAGTGGGAGT GATAGGAGCT ATGTTCCTTG GGTTCTTGGG    2040

AGCAGCAGGA AGCACTATGG GCGCAGCGTC AATAACGCTG ACGGTACAGG CCAGAAAACT   2100

ATTGTCTGGT ATAGTGCAAC AGCAGAACAA TCTGCTGAGA GCTATTGAGG CGCAACAGCA   2160

TCTGTTGCAA CTCACAGTCT GGGGCATCAA GCAGCTCCAG GCAAGAGTCC TGGCTGTGGA   2220

AAGATACCTA AGAGATCAAC AGCTCCTAGG GATTTGGGGT TGCTCTGGAA AACTCATTTG   2280

CACCACTACT GTGCCTTGGA ATACTAGTTG GAGTAATAAA TCTCTGGATA AGATTTGGAA   2340

TAACATGACT TGGATGGAGT GGGAAAGAGA AATTGACAAT TACACAAGCT TAATATACAC   2400

CTTACTTGAA GAATCGCAAA ACCAACAAGA AAAGAATGAA CAAGAGTTAT TGGAATTGGA   2460

TAAGTGGGCA AGTTTGTGGA ATTGGTTTAG CATAACAAAC TGGCTGTGGT ATATAAGAAT   2520

ATTCATAATG ATAGTAGGAG GCTTGATAGG TTTAAGAATA ATTTTTGCTG TGCTTTCTAT   2580

AGTAAATAGA GTTAGGCAGG GATACTCACC ATTATCATTT CAGACCCTCA TCCCAGCCCA   2640

GAGGGGACCC GACAGGCCCG AAGGAATCGA AGAAGGAGGT GGAGAGAGAG ACAGAGACAG   2700

ATCCACTCGA TTAGTGAACG GATTCTTAGC ACTGTTCTGG GACGATCTTC GGAGCCTGTG   2760

CCTCTTCAGC TACCACCGCT TGACAGACTT ACTCTTGATT GTAGCGAGGA TTGTGGAACT   2820

TCTGGGACGC AGGGGGTGGG AAGTCCTCAA ATATTGGTGG AATCTCCTGC TGTATTGGAG   2880

TCAGGAACTA AAGAATAGTG CTGTTAGCTT GCTCAACGCC ACAGCTATAG CAGTAGCTGA   2940

AGGGACAGAT AGGGTTATAG AAGTAGTACA AAGAGTGGGT AGAGCTATTC TCCACATACC   3000

TACAAGAATA AGACAGGGCT TTGAAAGGGC TTTGCTATAA GATGGGTGGC AAGTGGTCAA   3060

AAAGTAAAAT GGGATGGCCT GCTGTAAGGG AAAGAATGAA GCGAGCTGAG CCAGCAGCAG   3120

ATGGGGTGGG AGCAGCATCT AGAGACCTGG AAAAACATGG AGCACTCACA AGTAGCAATA   3180

CAGCAGCTAC TAATGCTGAT TGTGCCTGGC TAGAAGCACA AGAGGATGAG GAGGTGGGTT   3240

TTCCAGTCAA ACCTCAGGTA CCTTTAAGAC CAATGACTTA CAAAGCAGCT TTAGATCTTA   3300

GCCACTTTTT AAAAGAAAAG GGGGGACTGG AAGGGCTAGT TTACTCCCAA AAAAGACAAG   3360

ATATCCTTGA TCTGTGGATC TACCACACAC AAGGCTACTT CCCTGATTGG CAGAACTACA   3420

CACCAGGGCC AGGGGTCAGA TTTCCACTGA CCTTTGGATG GTGCTTCAAG TTAGTACCAG   3480

TAGAGCCAGA GAAAGTAGAA GAGGCCAATG AAGGAGAGAA CAACAGCTTG TTACACCCTA   3540

TGAGCCTGCA TGGGATGGAG GACCCGGAGA AAGAAGTGTT AGTGTGGAAG TTTGACAGCC   3600

ACCTAGCATT TCGTCACATG GCCCGAGAGC TGCATCCGGA GTACTACAAA GACTGCTGAC   3660

ATCGAGTTTT CTACAAGGGA CTTTCCGCTG GGACTTTCC AGGGGAGGCG TGGCCTGGGC    3720

GGGACTGGGG AGTGGCGAGC CCTCAGATGC TGCATATAAG CAGCTGCTTT TTGCCTGTAC   3780

GGGGTCTCTC TGGTTAGACC AGATCTGAGC CTGGAGCTC TCTGGCTAAC TAGGGAACCC    3840

ACTGCTTAAG CCTCAATAAA GCTTGCCTTG AGTGCTTCAA GTAGTGTGTG CCCGTCTGTT   3900
```

-continued

| | | | | | |
|---|---|---|---|---|---|
| GTGTGACTCT | GCTATCTAGA | GATCCCTCAG | ACCCTTTTAG | TCAGTGTGGA | AAATCTCTAG | 3960 |
| CAATATATAA | ATATATCTTT | GACCTTTACA | GCATATGGTA | ATAACTTAAA | AATTATATGC | 4020 |
| CTAATTGTGA | AAAAAAAAAA | AGAAAAAAGA | ACTCTTCTTG | CCAGAATCCA | AGTCCCATGA | 4080 |
| AAGTAGCCAA | TGCTGTCTCA | TTAGTTAGTA | AGCTAATGGA | AATGTTGCCA | GCATTTCTTT | 4140 |
| CAGTGTCTAG | AAAACAGAGT | GTGCAATGTG | CCAAGTCTTC | ACTGATTTAT | TTTTGTAAGC | 4200 |
| AGCAGTGTAA | TAAACCCAAA | GAAGCCAAAA | AAGCAAATTT | TTAAAAAATA | AATATTCATT | 4260 |
| TGCTATCAAG | ATGGGTATGA | CCTTTTTACC | CAAGCCTATT | ACTGACAATT | CAGAAAGACT | 4320 |
| ATGTGAAATA | GTCACTCATT | TATCTTAATT | GCATTTGCAG | GTACTACCAC | CACTCAAGTT | 4380 |
| TTAAAATGTT | TTTAAACACT | CAAGTTTGCA | TTCCTTTAGC | TTTTATACAA | GAAACCACAT | 4440 |
| TATTTTACAT | ACATATTAAT | TATTTTCTGA | CCTTTCAGGA | AAACCCAATA | ATATAAATCT | 4500 |
| ACAAAATGAA | ATAATACTCA | AGAATTC | | | | 4527 |